(12) United States Patent
Cameron et al.

(10) Patent No.: US 11,364,220 B2
(45) Date of Patent: *Jun. 21, 2022

(54) COMPOUNDS AND METHODS FOR INHIBITING CPY26 ENZYMES

(71) Applicant: Queen's University at Kingston, Kingston (CA)

(72) Inventors: Donald Andrew Cameron, Amherstview (CA); Martin Petkovich, Kingston (CA); Toni Kristian Rantanen, Burlington (CA); Victor Snieckus, Kingston (CA); Johnathan Board, Vaughan (CA); Suneel Singh, Kingston (CA); Ashishkumar Jayantilal Maheta, Mississauga (CA)

(73) Assignee: Queen's University at Kingston, Kingston (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/105,572

(22) Filed: Nov. 26, 2020

(65) Prior Publication Data
US 2021/0220326 A1 Jul. 22, 2021

Related U.S. Application Data

(63) Continuation of application No. 16/469,387, filed as application No. PCT/CA2017/051510 on Dec. 13, 2017, now Pat. No. 10,874,634.

(60) Provisional application No. 62/434,082, filed on Dec. 14, 2016.

(51) Int. Cl.
| | | |
|---|---|---|
| *A61K 31/353* | (2006.01) | |
| *A61K 31/07* | (2006.01) | |
| *A61K 31/145* | (2006.01) | |
| *A61K 31/167* | (2006.01) | |
| *C07C 233/81* | (2006.01) | |
| *C07C 311/21* | (2006.01) | |
| *C07D 311/70* | (2006.01) | |

(52) U.S. Cl.
CPC ............ *A61K 31/353* (2013.01); *A61K 31/07* (2013.01); *A61K 31/145* (2013.01); *A61K 31/167* (2013.01); *C07C 233/81* (2013.01); *C07C 311/21* (2013.01); *C07D 311/70* (2013.01)

(58) Field of Classification Search
CPC .... A61K 31/353; A61K 31/07; A61K 31/145; A61K 31/167; C07C 233/81; C07C 311/21; C07D 311/70
USPC ....................................................... 514/456
See application file for complete search history.

(56) References Cited

U.S. PATENT DOCUMENTS 10,874,634 B2 12/2020 Cameron et al.

FOREIGN PATENT DOCUMENTS

CA 2238274 A1 5/1997

OTHER PUBLICATIONS

Cancer [online], [retrieved on Jul. 6, 2007] Retrieved from the Internet, URL: http://Avww.nim.nih.gov/medlineplus/cancer.html (Year: 2007).*
Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*
International Search Report and Written Opinion for corresponding international application No. PCT/CA2017/05150 filed on Dec. 13, 2017.
Takagi, K. et al., "Inhibition of omithine decarboxylase induction by retinobenzoic acids in relation to their binding affinities to cellular retinoid-binding proteins", J. Cancer Res. Clin. Oncol., vol. 114, pp. 221-224, (1988).
Wouters, W., et al., "Effects of Liarozole, a New Antitumoral Compound, on Retinoic Acid-induced inhibition of Cell Growth and on Retinoic Acid Metabolism in MCF-7 Human Breast Cancer Cells", Cancer Research, vol. 52, pp. 2841-2846, (1992).
Beckenbach, L., et al., "Retinoid Treatement of Skin Diseases", Eur J Dermatol., vol. 25(5) pp. 384-391, (2015).
Chang, Y-C., et al., "Effect of Oral 13-Cis-Retinoic Acid Treatment on Postoperative Clinical Outcome of Eyes With Proliferative Vitreoretinopathy", American Journal of Ophthamology, vol. 146, No. 3, pp. 441-446, (2008).
Chen, S., et al., "Effect of all-trans-retinoic acid on enterovirus 71 infection in vitro", British Journal of Nutrition, 111, 1586-1593, (2014).
Connolly, R.M., et al., "Molecular Pathways: Current Role and Future Directions of the Retinoic Acid Pathway in Cancer Prevention and Treatment", Clin Cancer Res; 19(7), pp. 1651-1659, (2013).
Das, B.C., et al., "Retinoic acid signaling pathways in development and diseases", Bioorganic & Medicinal Chemistry, vol. 22, pp. 673-683, (2014).
Esteves, M. et al.,"Retinoicacid-loaded Polymeric Nanoparticles Induce Neuroprotection in a mouse model for Parkinson's disease", Frontiers in Aging Neuroscience, vol. 7, pp. 1-10, (2015).

(Continued)

*Primary Examiner* — Kristin A Vajda
(74) *Attorney, Agent, or Firm* — Angela Lyon

(57) ABSTRACT

Compounds described herein are inhibitors of retinoic add inducible P450 (CYP26) enzymes, and are useful for treating diseases that are responsive to retinoids. Certain compounds have retinoid activity, are resistant to CYP26-mediated catabolism, and are used for treating diseases that are responsive to retinoids.

20 Claims, 7 Drawing Sheets

(56) References Cited

OTHER PUBLICATIONS

Freemantle, S. J., et al., "Retinoids in cancer therapy and chemoprevention: promise meets resistance", Oncogene, vol. 22, pp. 7305-7315, (2003).
He, Y. et al., "The role of retinoic acid in hepatic lipid homeostasis defined by genomic binding and transcriptome profiling", BMC Genomics, vol. 14, 575, pp. 1-11, (2013).
Lu, L., et al., "Critical role of all-trans retinoic acid in stabilizing human natural regulatory T cells under inflammatory conditions", PNAS, pp. E3432-E3440, (2014).
Medh, R.D., et al., "Stimulation of Tissue Plasminogen Activator Production by Retinoic Acid: Synergistic Effect on Protein Kinase C-Mediated Activation", Blood, pp. 1-16, (1992).
Selek, H. et al., "Evaluation of retinoic acid ophthalmic emulsion in dry eye", European Journal of Ophthalmology. vol. 10, No. 2, pp. 121-127, (2000).
Shimono, K. et al., "Potent inhibition of heterotopic ossification by nuclear retinoic acid receptor-γ agonists", Nature Medicine, vol. 17, No. 4, pp. 454-461, (2011).
Yim, C.Y., et al., "Headway and Hurdles in the Clinical Development of Dietary Phytochemicals for Cancer Therapy and Prevention: Lessons Learned from Vitamin A Derivatives", The AAPS Journal, vol. 16, No. 2, pp. 281-288, (2014).

\* cited by examiner

COMPOUNDS AND METHODS FOR INHIBITING CPY26 ENZYMES

RELATED APPLICATION

This application claims the benefit of the filing date of U.S. Provisional Patent Application No. 62/434,082 filed on Dec. 14, 2016, the contents of which are incorporated herein by reference in their entirety.

FIELD OF THE INVENTION

The invention relates to compounds that inhibit certain cytochrome P450 enzymes (P450RAI), which are known as CYP26. The invention also relates to compounds that have retinoid-like activity.

BACKGROUND

Vitamin A metabolism gives rise to several active forms of retinoic acid (RA) which are involved in regulating gene expression during development, regeneration, and in the growth and differentiation of epithelial tissues. Vitamin A metabolism has been linked to apoptosis (i.e., programmed cell death) in a number of cell types, and has been shown to have anti-carcinogenic and anti-tumoral properties. Early studies of retinol deficiency indicated a correlation between vitamin A depletion and a higher incidence of cancer and increased susceptability to chemical carcinogenesis. Several animal models have been used to demonstrate the effectiveness of retinoids in suppressing carcinogenesis in a variety of tissues including skin, mammary epithelia, oral cavity, aerodigestive tract, liver, bladder and prostate. These studies have led to the preventative use of retinoids in the treatment of premalignant lesions, as well as in the prevention of secondary tumours (e.g., prevention of recurrence of non-small cell lung carcinomas and basal cell carcinomas). RA itself has been found to be useful therapeutically, notably in the treatment of cancers. Studies have shown that cytochrome P450 inhibitors that block RA metabolism, result in increased levels of RA, which may be useful therapeutic agents in the treatment of cancer (Wouters W., et al., *Cancer Res* (1992) 52:2841-6). Thus RA metabolizing cytochrome P450s may be useful targets for the treatment of a number of different types of cancer.

SUMMARY OF THE INVENTION

An aspect of the invention provides a compound of formula (1)

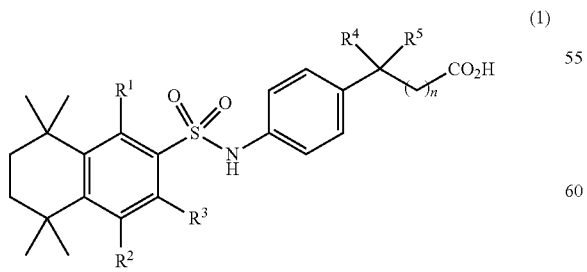

where $R^1$, $R^2$, and $R^3$ are independently H or $C_1$-$C_4$, $R^4$ and $R^5$ are independently H or $C_1$, and n is 0 to 4. In some embodiments of this aspect wherein $R^1$ and $R^2$ are H, $R^3$ is methyl. In some embodiments of this aspect, n is 1. In some embodiments of this aspect, $R^4$ and $R^5$ are methyl. In some embodiments, $R^4$ and $R^5$ are each $C_1$ and they form a ring.

In some embodiments of this aspect, the compound of formula (1) is

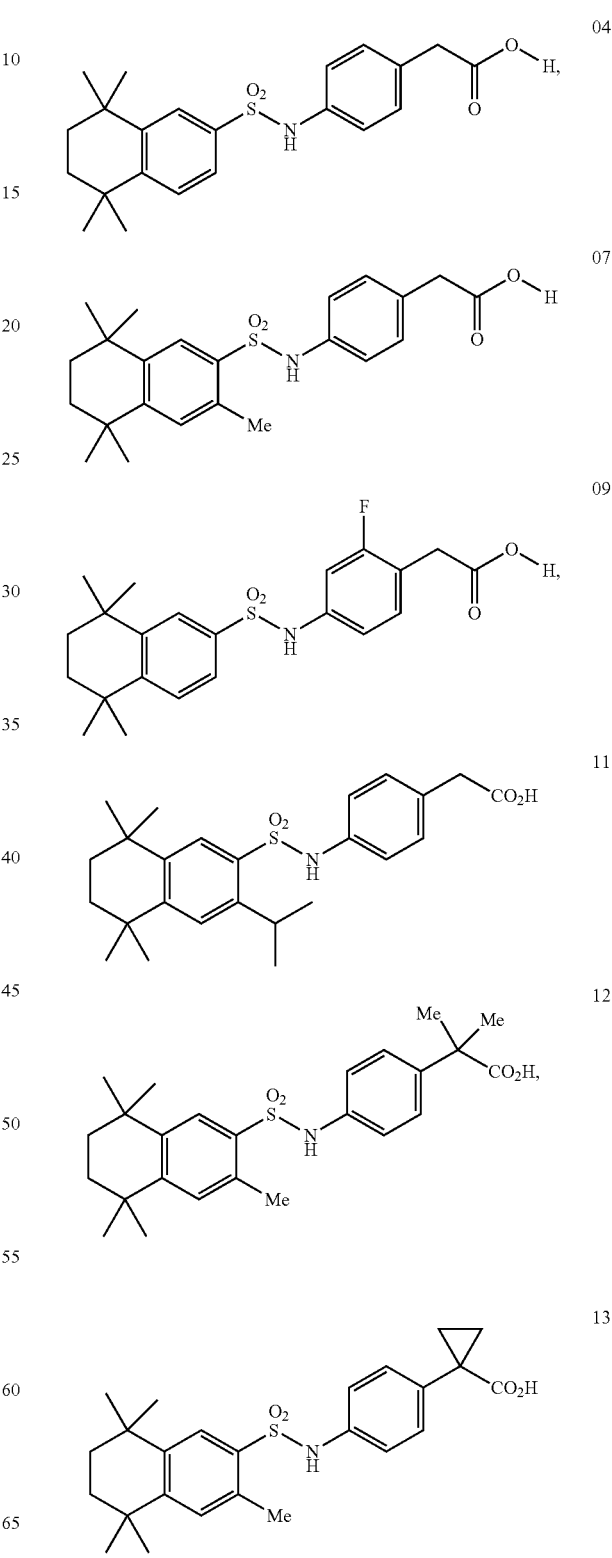

-continued

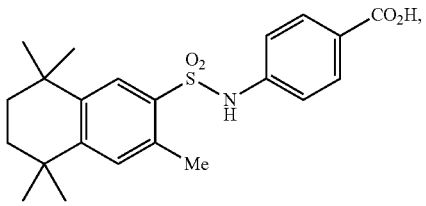
14

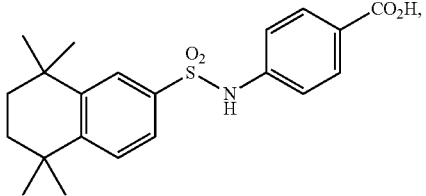
15

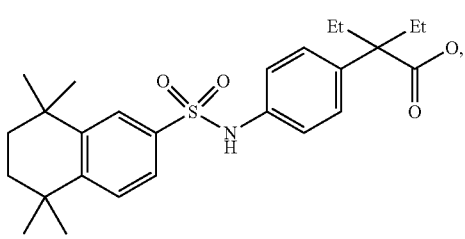
17

18

19

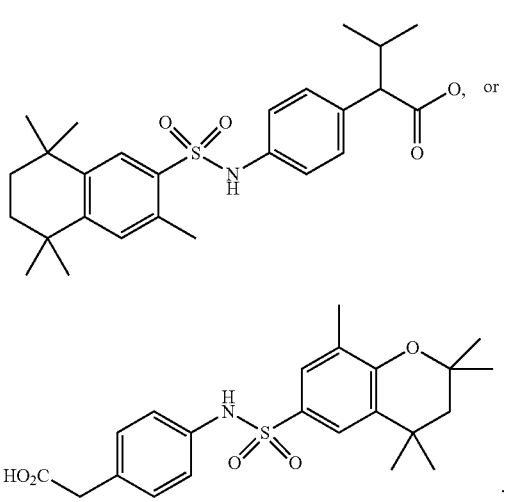
21

In another aspect, the invention provides a method of treating a disease or condition in a mammal, comprising administering an inhibitor of the breakdown of RA, comprising a compound of Formula (1).

In yet another aspect, the invention provides a method of treating a disease or condition in a mammal, comprising administering an inhibitor of the breakdown of RA, comprising a compound of Formula (1). In some embodiments of this aspect, the disease or condition is a skin disease. In certain embodiments of this aspect, the skin disease is actinic keratosis, arsenic keratosis, inflammatory and non-inflammatory acne, psoriasis, ichthyosis and other keratinization, hyperproliferative disorders of the skin, eczema, atopic dermatitis, Darriers disease, lichen planus, glucocorticoid damage, or steroid atrophy. In some embodiments of this aspect, the compound is applied as a topical antimicrobial, a skin anti pigmentation agent, to treat and reverse the effects of age and photo damage to the skin. In an embodiment of this aspect, the method of treating a disease or condition in a mammal further comprises preventing cancerous or precancerous conditions. In some embodiments of this aspect, the condition is premalignant or malignant hyperprolifertive diseases, cancer of the breast, skin, prostate, cervix, uterus, colon, bladder, esophagus, stomach, lung, larynx, oral cavity, blood, lymphatic system, metaplasias, dysplasias, neoplasias, leukoplasias, or papillomas of the mucous membranes, or Kaposi's sarcoma. In some embodiments of this aspect, the compound is useful to treat diseases of the eye comprising prolieferative vitreoretinopathy (PVR), retinal detachment, dry eye, corneopathies. In some embodiments of this aspect, the compound is useful to treat cardiovascular disease.

In some embodiments of this aspect, the cardiovascular disease comprises diseases associated with lipid metabolism, dyslipidemias, prevention of post-angioplasty restenosis. In some embodiments of this aspect, the compound is useful as an agent to increase the level of circulating tissue plasminogen activator (TPA), or to treat or prevent conditions and diseases associated with human papilloma virus (HPV), inflammatory disease such as pulmonary fibrosis, ileitis, colitis and Crohn's disease, neurodegenerative disease such as Alzheimer's disease, Parkinson's disease, stroke, improper pituitary function including improper production of growth hormone, modulation of apoptosis including both the induction of apoptosis, and inhibition of T-cell activated apoptosis, restoration of hair growth, diseases associated with the immune system, modulation of organ transplant rejection, facilitation of wound healing. In some embodiments of this aspect, the compound is useful in treating type II non-insulin dependent diabetes mellitus, disorders of ectopic bone formation, or muscle tissue calcification. In some embodiments of treating a disease or condition, a medicament is administered as a powder, spray, pill, tablet, syrup, elixir, solution or suspension capable of being administered by injection, suppository, extended release formulation for deposit under the skin or intramuscular injection. In some embodiments, a compound of formula (1) is included in a medicament for topical application in a formulation comprising between 0.01 milligrams and 1 mg per mL of the compound. In other embodiments, a compound of formula (1) is included in a medicament for systemic administration in a formulation comprising between 0.01 and 5 mg per kg body weight per day.

In another embodiment of the above method aspect, the compound of Formula (1) is given in combination with a retinoid or a retinoid precursor. In some embodiments, the retinoid or a retinoid precursor is selected from retinol, retinaldehyde, RA, or other natural or synthetic retinoids. In some embodiments, the compounds are provided as a combination in the same tablet, capsule, injectable, or topical formulation.

In yet another aspect, the invention provides use of the compound of formula (1) in the treatment of skin disease. In certain embodiments of this aspect, the skin disease is actinic keratosis, arsenic keratosis, inflammatory and non-inflammatory acne, psoriasis, ichthyosis and other keratinization, hyperproliferative disorders of the skin, eczema, atopic dermatitis, Darriers disease, lichen planus, glucocorticoid damage, or steroid atrophy. In some embodiments of this aspect, the compound is applied as a topical antimicrobial, a skin anti pigmentation agent, to treat and reverse the effects of age and photo damage to the skin. In certain embodiments of this aspect, the compound of formula (1) is useful for treatment or prevention of cancerous or precancerous conditions. In certain embodiments of this aspect, the condition is premalignant or malignant hyperprolifertive diseases, cancer of the breast, skin, prostate, cervix, uterus, colon, bladder, esophagus, stomach, lung, larynx, oral cavity, blood, lymphatic system, metaplasias, dysplasias, neoplasias, leukoplasias, or papillomas of the mucous membranes, or Kaposi's sarcoma. In certain embodiments of this aspect, the compound is useful to treat diseases of the eye comprising prolieferative vitreoretinopathy (PVR), retinal detachment, dry eye, corneopathies. In certain embodiments of this aspect, the compound is useful to treat cardiovascular disease. In certain embodiments of this aspect, the cardiovascular disease comprises diseases associated with lipid metabolism, dyslipidemias, prevention of post-angioplasty restenosis. In certain embodiments of this aspect, the compound is useful as an agent to increase the level of circulating tissue plasminogen activator (TPA), or to treat or prevent conditions and diseases associated with human papilloma virus (HPV), inflammatory disease such as pulmonary fibrosis, ileitis, colitis and Crohn's disease, neurodegenerative disease such as Alzheimer's disease, Parkinson's disease, stroke, improper pituitary function including improper production of growth hormone, modulation of apoptosis including both the induction of apoptosis, and inhibition of T-cell activated apoptosis, restoration of hair growth, diseases associated with the immune system, modulation of organ transplant rejection, facilitation of wound healing. In certain embodiments of this aspect, the compound is useful in treating type II non-insulin dependent diabetes mellitus, disorders of ectopic bone formation, or muscle tissue calcification.

In another aspect, the invention provides use of a formulation comprising one or more compounds of Formula (1) in a mixture with a pharmaceutically acceptable excipient.

In certain embodiments of this aspect, the formulation being adapted for administration to a mammal, to treat or alleviate a condition that is treatable by retinoids, or which is controlled by or responsive to the organism's native RA. In some embodiments, the formulation is administered as a powder, spray, pill, tablet, syrup, elixir, solution or suspension capable of being administered by injection, suppository, extended release formulation for deposit under the skin or intramuscular injection.

In another aspect, the invention provides use of a compound of formula (1) in a medicament in a formulation between 0.01 milligrams and 1 mg per mL for topical application.

In yet another aspect, the invention provides use of a compound of formula (1) in a medicament in a formulation between 0.01 and 5 mg per kg body weight per day for systemic administration.

BRIEF DESCRIPTION OF THE DRAWINGS

For a better understanding of the invention and to show more clearly how it may be carried into effect, reference will now be made by way of example to the accompanying drawings, which illustrate aspects and features according to preferred embodiments of the invention, and in which.

DETAILED DESCRIPTION OF THE INVENTION

Definitions

Figure 1:
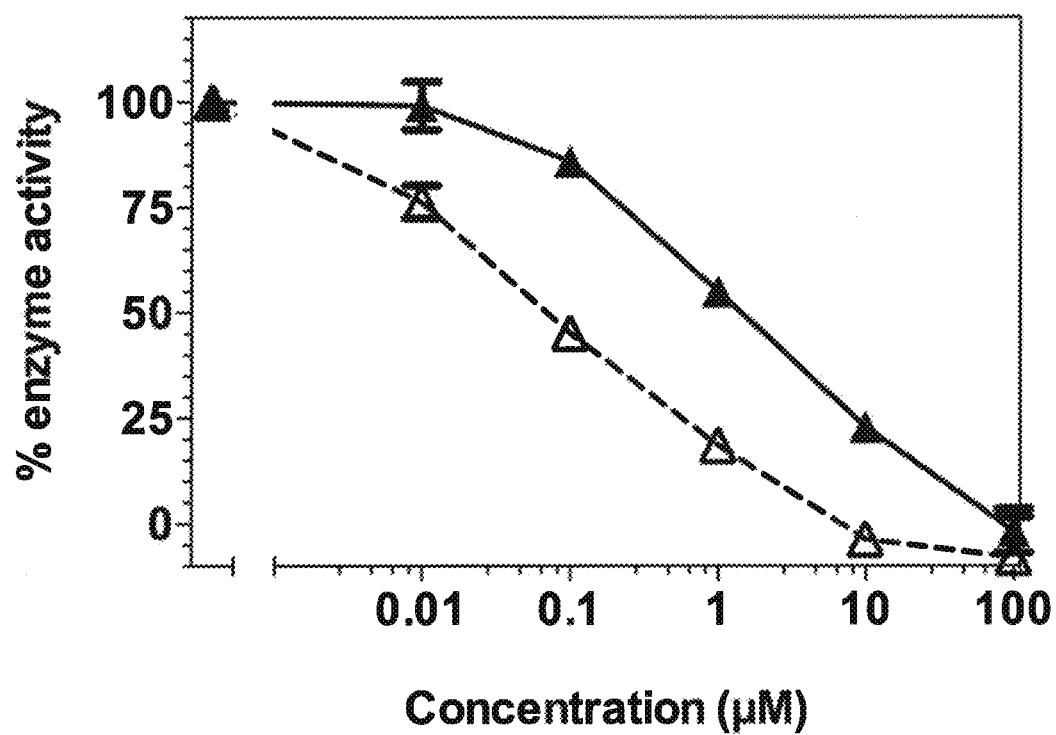
FIG. 1 shows a plot of activity of CYP26A1 enzyme in the presence of increasing concentration of compound 12 (Δ) versus ketoconazole (▲).

As used herein, the term "RA" refers to retinoic acid.

As used herein, the term "a.k.a." or "aka" refers to also known as.

As used herein, the term "MEM" refers to minimum essential medium (available from Sigma-Aldrich, Oakville, Canada).

As used herein, the term "FBS" refers to fetal bovine serum.

As used herein, the term "QPCR" refers to quantitative polymerase chain reaction.

As used herein, the term "DCE" refers to 1,2-dichloroethane.

As used herein, the term "DMSO" refers to dimethylsulphoxide.

As used herein, the term "CYP26" refers to a subfamily of cytochrome P450 enzymes which are specific in the metabolism of retinoic acid.

As per the custom of the field of this invention, the characters "CYP26A1" and "CYP26B1" can refer to the enzyme as well as to the gene that encodes the enzyme; typically genes are noted in italics, i.e., CYP26A1 gene encodes the CYP26A1 enzyme (protein). Accordingly, as used herein, the terms "CYP26A1" and "CYP26B1" refer to distinct genes that encode members of the cytochrome P450 family of enzymes, and the terms "CYP26A1" and "CYP26B1" refer to the enzyme (protein) products of their respective genes.
Embodiments Several compounds having retinoid-like activity are marketed under appropriate regulatory approvals in the United States and elsewhere as medications for the treatment of diseases that are responsive to retinoids. Retinoic acid (RA) itself is a natural product, biosynthesized and present systemically in circulation and in a multitude of human and mammalian tissues and is known to play an important role in the regulation of gene expression, tissue differentiation and maintenance, and other important biological processes in mammals including humans. A natural catabolic pathway in mammals, including in humans, of RA includes a hydroxylation step catalyzed by the CYP26 family of enzymes, including CYP26A1, CYP26B1 and CYP26C1. Several inhibitors of CYP26A1 have been synthesized or discovered previously including liarazole, ketoconazole, and R116010 (see Table 1 for structural information). It has also been noted that administration to mammals of inhibitors of CYP26 results in significant increase of systemic and or local RA levels, and that treatment with CYP26 inhibitors, for example with liarazole, gives rise to effects similar to treatment by retinoids, for example amelioration of psoriasis.

Some embodiments of the invention provide compounds that act as inhibitors with a bias of inhibition of CYP26A1 over CYP26B1. Accordingly, such compounds have the potential to provide therapeutic benefit in the treatment of, or prevention of, diseases that respond to synthetic or natural retinoids (such as RA). The perceived mode of action of these compounds is that by inhibiting CYP26A1 that catabolizes natural RA, endogenous levels of RA are permitted to rise to a level where desired therapeutic benefits are attained. In some embodiments, the CYP26A1 gene is directly regulated (i.e., expression is increased) by RA itself; blocking CYP26A1 enzyme activity leads to increased CYP26A1 expression.

Compounds of Formula (1), shown below, are useful for prevention or treatment of diseases or conditions in mammals, including humans, in instances where such diseases and conditions are prevented, treated, ameliorated, or disease onset is delayed by the administration of retinoid compounds or by the organism's naturally occurring RA. Compounds of Formula (1) inhibit the breakdown of RA, embodiments of the invention relate to use of compounds of Formula (1) as single agent therapies. Other embodiments relate to use of compounds of Formula (1) in conjunction with RA or other retinoids. Such inhibitory compounds are represented by general Formula (1):

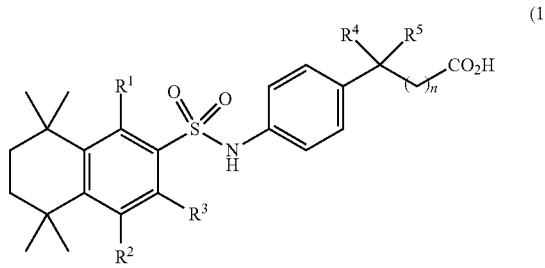

where $R^1$, $R^2$, and $R^3$ are independently H or $C_1$-$C_4$;
$R^4$ and $R^5$ are independently H or $C_1$;
n is 0 to 4.

Structural formulae for compounds described herein including precursors of compounds of Formula (1) are provided in Table 1. Synthetic methodologies are described in the Working Examples. Certain compounds were studied to quantify activity and determine if they inhibit CYP26A1. Such compounds are listed in Table 2.

Figure 3:
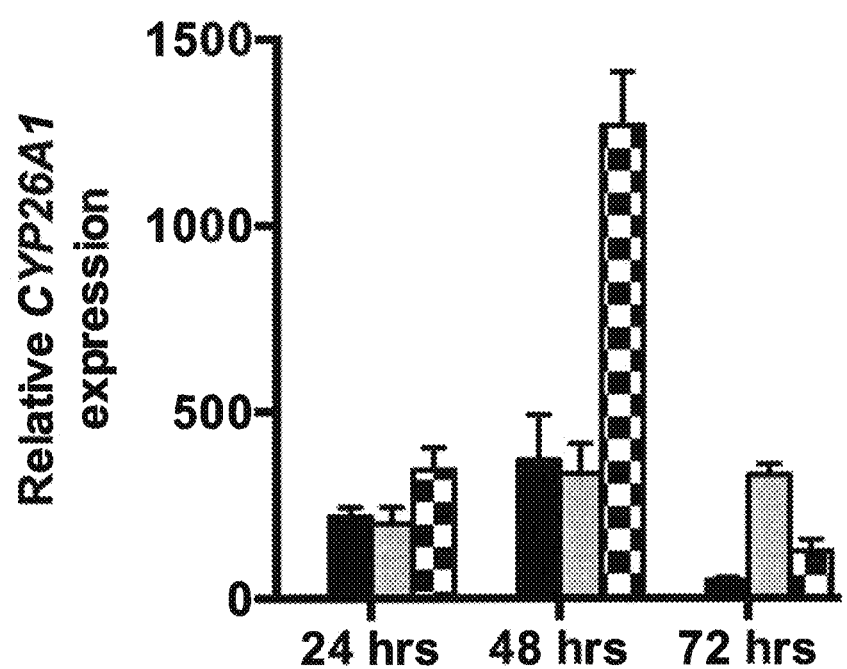
FIG. 3 shows a bar graph of QPCR analysis of CYP26A1 expression in MCF-7 cells treated with vehicle (DMSO, white bars), 1 μM RA (black bars), 1 μM RA+1 μM ketoconazole (gray bars), or 1 μM RA+1 μM compound 12 (checkered bars) for either 24, 48 or 72 hours.
Figure 4:
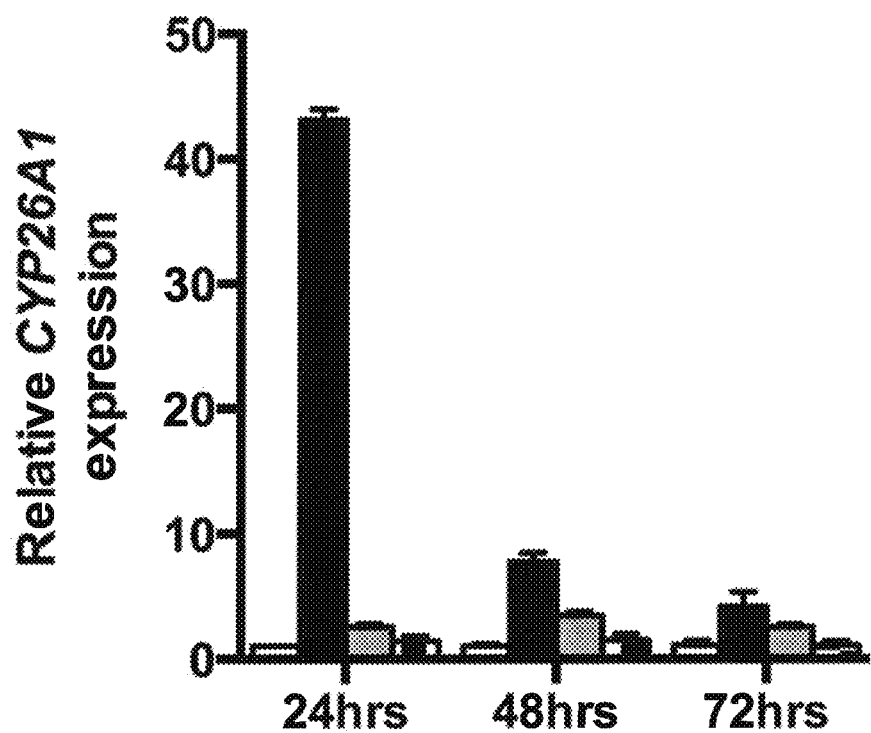
FIG. 4 shows a bar graph of QPCR analysis of CYP26A1 expression in MCF-7 cells treated with either vehicle (DMSO, white bars), 0.1 μM RA (black bars), 1 μM ketoconazole (gray bars) or 1 μM compound 12 for 24, 48 or 72 hours.

Various embodiments of the invention are directed to compounds that exhibit one or more of inhibition of CYP26A1, resistance to CYP26, and retinoid activity. Compounds of the invention that have an inhibitory effect on CYP26A1 include compounds of Formula (1). Several such compounds exhibit selective inhibitory activity towards CYP26A1, including compounds 2, 4, 6, 7, 12, 16, 19, and 21. These compounds inhibit CYP26A1-mediated RA metabolism with activities comparable to or better than ketoconazole (see IC50 values in Table 2). None of the above compounds inhibited the CYP26B1 enzyme, indicating that these structures are highly specific to CYP26A1. Importantly, no retinoid activity was observed for any of the compounds tested (see Luciferase data in Table 3, and qPCR data in FIG. 4). However, addition of compound 12 in combination with RA indicated that CYP26A1 inhibition could greatly enhance RA signaling in MCF-7 cells. This was assessed by induction of CYP26A1 expression, which is a highly sensitive RA target gene (see FIG. 3). Together, these data support a mechanism of action whereby the described compounds effectively block CYP26A1-mediated RA metabolism to allow the buildup of active RA, and enhancement of RA signaling.

Figure 6:
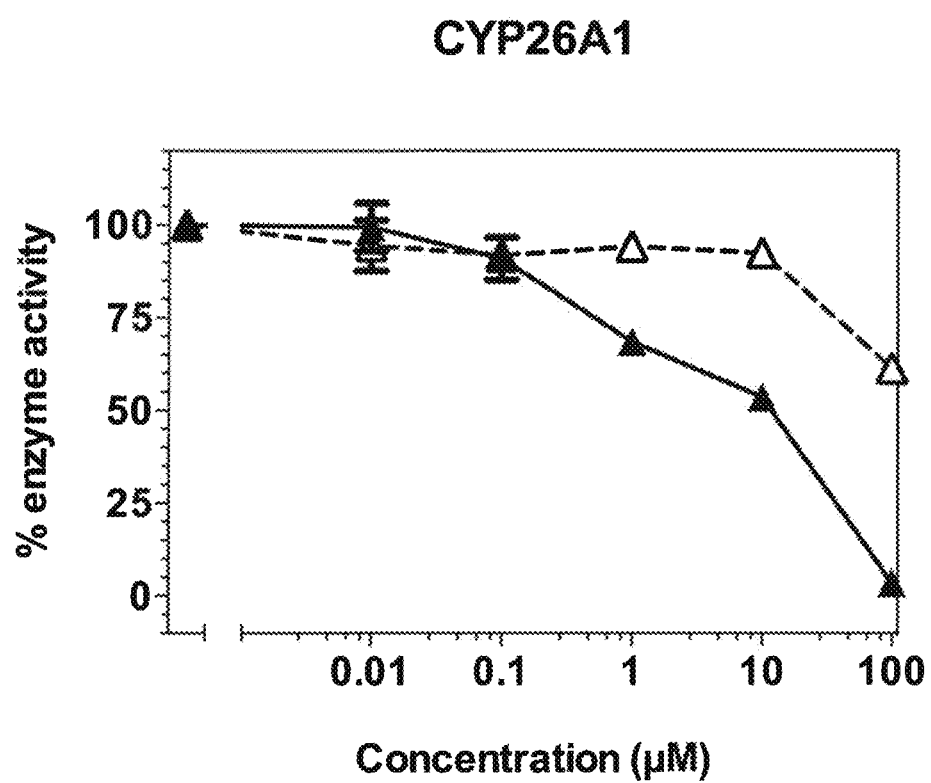
FIG. 6 shows a plot of activity of CYP26A1 enzyme in the presence of increasing concentration of compound 15 (Δ) versus ketoconazole (▲).
Figure 7:
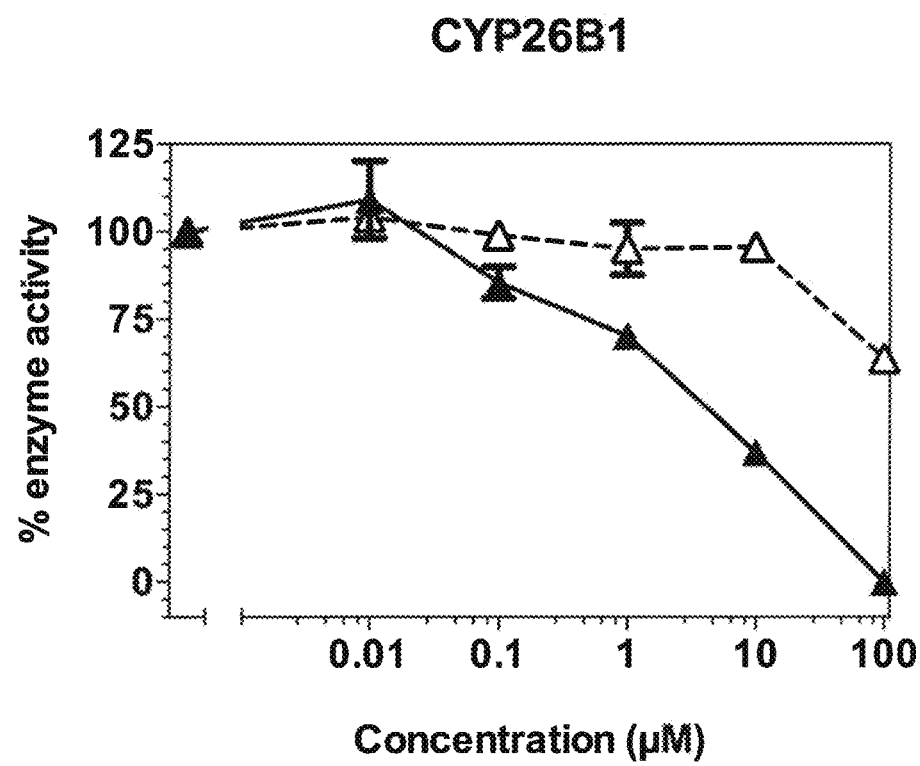
FIG. 7 shows a plot of activity of CYP26B1 enzyme in the presence of increasing concentration of compound 15 (Δ) versus ketoconazole (▲).
Figure 8:
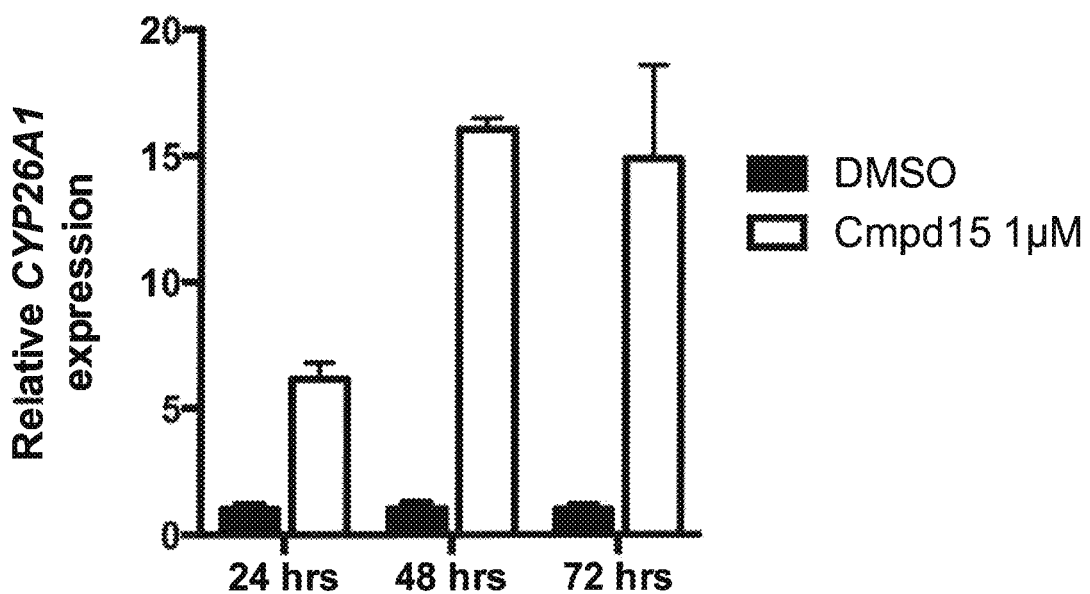
FIG. 8 shows a bar graph of QPCR analysis of CYP26A1 expression in MCF-7 cells treated with either vehicle (DMSO, black bars), or 1 μM compound 15 for 24, 48 or 72 hours.

Compound 15 is a related structure, but does not exhibit any inhibitory activity against either CYP26A1 (FIG. 6) or CYP26B1 enzymes (FIG. 7). However, this compound does exhibit retinoid-like activity (FIG. 8). Compound 15 induces expression of the RA target gene CYP26A1 in MCF-7 cells, suggesting that it can function as a CYP26-resistant retinoid.

Embodiments may be useful in the treatment of skin diseases including but not limited to: actinic keratosis, arsenic keratosis, inflammatory and non-inflammatory acne, psoriasis, ichthyosis and other keratinization and hyperproliferative disorders of the skin, eczema, atopic dermatitis, Darriers disease, lichen planus, prevention and reversal of glucocorticoid damage (steroid atrophy).

In some embodiments, a compound of Formula (1) may be applied as a topical antimicrobial, as skin anti pigmentation agents, and to treat and reverse the effects of age and photo damage to the skin. In other embodiments a compound of Formula (1) may be administered through another route of administration (e.g., orally, intravenous, etc.) for the desired effect. Systemically, such compounds would target one CYP26 subtype selectively. Embodiments are also useful for the treatment or prevention of cancerous and precancerous conditions including premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplasias, and papillomas of the mucous membranes and in the treatment of Kaposi's sarcoma. In addition, embodiments may be used to treat diseases of the eye including, but not limited to, prolieferative vitreoretinopathy (PVR), retinal detachment and dry eye and other corneopathies, as well as in the treatment and prevention of various cardiovascular diseases including, but not limited to, diseases associated with lipid metabolism such as dyslipidemias, prevention of post-angioplasty restenosis, and as an agent to increase the level of circulating tissue plasminogen activator (TPA). Other uses for a compound as described herein include the treatment and prevention of conditions and diseases associated with human papilloma virus (HPV) including warts and genital warts, various inflammatory diseases such as pulmonary fibrosis, ileitis, colitis and Crohn's disease, neurodegenerative disease such as Alzheimer's disease and Parkinson's disease and stroke, improper pituitary function including improper production of growth hormone, modulation of apoptosis including both the induction of apoptosis, and inhibition of T-cell activated apoptosis, restoration of hair growth, including combination therapies with the present compounds and other agents such as Minoxidil, diseases associated with the immune system including the use of the current compounds as immunosuppressants and immunostimulants, modulation of organ transplant rejection and facilitation of wound healing including modulation of chelosis. Embodiments may also be useful in treating type II non-insulin dependent diabetes mellitus, fibrosis of the liver, as well as in disorders of ectopic bone formation such as cardiovascular calcification and muscle tissue calcification.

Other embodiments of the invention relate to a pharmaceutical formulation comprising one or more compounds of Formula (1) in a mixture with pharmaceutically acceptable excipient or carrier, said formulation being adapted for administration to a mammal, including a human, to treat or alleviate a condition described above, or which is controlled by or responsive to native RA. A formulation as described herein may include a retinoid, for example, a co-administration with a retinoid to enhance or prolong the effects of medications containing a retinoid and/or of native RA.

In various embodiments, a pharmaceutical composition may be administered topically or systemically, depending on considerations such as: the condition to be treated; need for site-specific treatment; and quantity of drug to be administered, etc. For example, in the treatment of dermatoses, it generally is preferable to administer the drug topically. Although for treatment of severe acne or psoriasis, oral administration may also be used. Any common topical formulation such as a solution, suspension, gel, ointment, or salve and the like may be used. Preparations of such topical formulations are well described in the art of pharmaceutical formulations as exemplified by Remington's Pharmaceutical Science, Edition 17, Mack Publishing Company, Easton, Pa. For topical application, administration may be as a powder or spray, particularly in aerosol form. For systemic administration, it may be confected as a powder, pill, tablet or the like, or as syrup or elixir suitable for oral administration. Regarding co-administration of a compound of Formula (1) together with a retinoid or a retinoid precursor, the compounds could be provided as a combination in the same tablet, capsule, injectable, or topical formulation or they could be administered concurrently, for example one topically and the other orally. Examples of retinoid or a retinoid precursor include retinol, retinaldehyde, RA, and other natural or synthetic retinoids. For intravenous or intraperitoneal administration, the compound or combination of compounds may be prepared as a solution or suspension capable of being administered by injection. In certain cases, it may be useful to formulate a compound or combination of compounds in suppository form or as an extended release formulation for deposit under the skin or intramuscular injection.

One or more other agents and/or medicaments may be co-administered (e.g., administered simultaneously with, added to, or administered consecutively) with such topical formulation for such secondary purposes such as treating skin dryness, providing protection against light, treating dermatoses, treating or preventing infection, or reducing irritation, inflammation, and the like.

Treatment of dermatoses or any other indications known or discovered to be susceptible to treatment by retinoid acid-like compounds, or to control by naturally occurring retinoic acid will be effected or enhanced by administration of a therapeutically effective dose of one or more compounds of embodiments of the invention. A therapeutic concentration is that concentration which prevents, treats, ameliorates, reduces symptoms, delays onset, or slows or prevents proliferation of a disease or condition. In certain embodiments, the a compound may be used in a prophylactic manner to prevent onset of a particular condition.

A useful therapeutic or prophylactic concentration will vary from condition to condition and in certain cases may vary with the severity of the condition being treated and the patient's susceptibility to treatment. Accordingly, no single concentration will be uniformly useful, but will require modification depending on the particularities of the disease being treated. Such concentrations can be arrived at through routine experimentation and or routine procedures such as, for example, dose titration. However, it is expected that in treatment of, for example, acne, or similar dermatoses, a formulation between 0.01 milligrams and 1 mg per mL will constitute a therapeutically effective concentration for topical application. If administered systemically, an amount between 0.01 and 5 mg per kg body weight per day would be expected to effect a therapeutic result in the treatment of many diseases for which these compounds are useful.

In some embodiments, a CYP26 inhibitory compound of the invention may be co-administered with a formulation comprising one or more retinoid. Co-administration may include administration of the one or more retinoid simultaneously with, (e.g., added to) or consecutively (e.g., before or after) the inhibitory compound.

The following working examples further illustrate the present invention and are not intended to be limiting in any respect.

WORKING EXAMPLES

Example 1. Synthesis of Compounds

All chemical synthetic starting materials were purchased from Aldrich Chemical Company, TCI America, or Alfa Aesar and used without further purification. Solvents were freshly distilled over appropriate drying reagents. All experiments were carried out under a dry nitrogen atmosphere using standard Schlenk Techniques unless otherwise stated. Thin Layer Chromatography was carried out on $SiO_2$ (silica gel F254, Whatman). Flash chromatography was carried out on silica (silica gel 60, 70-230 mesh). $^1H$ and $^{13}C$ spectra were recorded on a $^1H$ and $^{13}C$ nuclear magnetic spectra (NMR) using a Bruker Avance 400 MHz spectrometer. Chemical shifts are reported in delta (δ) Table 1 units, expressed in parts per million (ppm) downfield from tetramethylsilane, using residual protonated solvent as an internal standard.

See Table 1 for structural formulae of numbered compounds.

Example 1A. Synthesis of Compounds that are Used to Prepare the Compounds of Formula (1), which Syntheses are Described in Example 1B Synthesis of Compound T-1

2,5-dimethyl-hexane-2,5-diol (10 g, 68.4 mmol) was placed in a reaction vessel with gentle stirring. Conc. HCl (aq, 80 mL) was added and the resulting mixture was stirred slowly for 15 mins. The resulting suspension was left standing for 2 h. It was then filtered and washed with 2×30 mL of water. A resulting solid was dried under high vacuum to afford the title compound T-1 (10.1 g, 81% yield). The analytical data matches those reported in the literature.

Synthesis of Compound T-2

In a 250 mL round-bottomed flask was weighed T-1 (11.0 g, 60 mmol). Dry benzene (240 mL) was added and then $AlCl_3$ (1.0 g, 7.5 mmol, 1.25 equiv) in portions. A resulting mixture was refluxed under argon for 16 h. The mixture was cooled to room temperature, and then poured on ice-water (500 mL). An organic layer was separated and an aqueous layer was extracted with $Et_2O$ (2×200 mL). Organics were combined, dried with $MgSO_4$, and solvent was evaporated under reduced pressure. A crude product residue was distilled under reduced pressure to afford the title compound T-2 as a colorless oil (10.0 g, 88% yield). The analytical data matches those reported in the literature.

Synthesis of Compound T-3

In a 50 mL round-bottomed flask was weighed T-2 (1.88 g, 10 mmol). Dry $CH_2Cl_2$ (12 mL) was added and then the resulting solution was cooled to 0° C. $Br_2$ (0.95 mL, 18.5 mmol, 1.8 equiv) was added dropwise. Then $BF_3$*THF complex (1.2 mL, 11 mmol, 1.1 equiv) dissolved in 2 mL $CH_2Cl_2$ was added dropwise. The mixture was stirred at room temperature under argon for 2 h, and then the reaction was quenched by the addition of water (10 mL). An organic layer was separated and an aqueous layer was extracted with $CH_2Cl_2$ (2×20 mL). The organics were combined, dried with $MgSO_4$ and the solvent was evaporated under reduced pressure. A crude product residue was purified via column chromatography to afford compound T-3 (2.5 g, 92%).

Synthesis of Compound T-4

In a 10 mL round-bottomed flask 1 mL of chlorosulfonic acid was added and cooled to 10° C. T-2 (0.5 g, 2.65 mmol) was added dropwise and the mixture warmed to room temperature. The dark reaction mixture was stirred for 2 h, then poured on ice-water, and extracted with $CH_2Cl_2$ (2×20 mL). The organic layer was dried ($MgSO_4$) and evaporated to afford T-4 as a dark oil, which was used directly without further purification.

Synthesis of Compound T-5

In a 50 mL round-bottomed flask T-3 (1.07 g, 4.0 mmol) was dissolved in dry THF (20 mL) under argon. The mixture was cooled to −78° C. and n-BuLi (10 M, 0.5 mL, 1.2 equiv) was added. The mixture was stirred for 30 mins at −78° C. and then crushed dry ice was added. The mixture was warmed to room temperature, then quenched with 10 mL $H_2O$. The THF was evaporated, then the reaction mixture extracted with $Et_2O$ (2×10 mL). The aqueous layer was acidified and extracted with EtOAc (2×20 mL). The organic layers were combined, dried ($MgSO_4$) and evaporated to afford compound T-5 (744 mg, 80%) which was used without further purification.

Synthesis of Compound T-6

In a 50 mL round-bottomed flask crude T-4 (2.7 mmol) was dissolved in $CH_2Cl_2$ (10 mL) under argon. 4-Amino-benzene acetic acid methyl ester (1 g, 2.2 equiv, 6.0 mmol) was added and the mixture was stirred for 1 h. Then pyridine (1 mL) was added and the mixture stirred for overnight at room temperature. After the reaction was complete, the volatiles were evaporated, $CH_2Cl_2$ (25 mL) added and the mixture washed with 1M NaOH (10 mL) followed by 1M HCl (10 mL). The organic layer was dried ($MgSO_4$) and evaporated. The residue was purified via column chromatography ($CH_2Cl_2$ to $CH_2Cl_2$/5% $Et_2O$) to afford T-6 (523 mgs, 47% (over two steps)).

Synthesis of Compound T-8

In a 250 mL round-bottomed flask was weighed T-1 (1.8 g, 10 mmol). Dry DCE (20 mL) was added followed by dry toluene (921 mg, 10 mmol, 1 equiv). Then AlCl3 (133 mg, 1 mmol, 10 mol %) was added in portions. The resulting mixture was stirred under argon for 16 h. The mixture was cooled to room temperature, and then poured on ice-water (50 mL). The organic layer was separated and the aqueous layer was extracted with $Et_2O$ (2×20 mL). The organics were combined, dried ($MgSO_4$) and the solvent was evaporated. The residue was purified via column chromatography (hexanes) to afford compound T-8 as a colorless oil (1.5 g, 76% yield).

Synthesis of Compound T-9

In a 10 mL round-bottomed flask 1 mL of chlorosulfonic acid was added and cooled to 10° C. Added was T-8 (0.5 g, 2.5 mmol) dropwise and the mixture was warmed to room temperature. The dark reaction mixture was stirred for 1 h and then poured on ice-water, and extracted with $CH_2Cl_2$ (2×20 mL). The organic layer was dried ($MgSO_4$) and evaporated to afford T-9 as a dark oil, which was used directly without further purification.

Synthesis of Compound T-10

In a 50 mL round-bottomed flask crude T-9 (750 mg, 2.5 mmol) was dissolved in $CH_2Cl_2$ (10 mL) under argon. 4-Aminobenzene acetic acid methyl ester (1 g, 2.4 equiv, 6.0 mmol) was added and the mixture was stirred for 1 h. Then pyridine (1 mL) was added and the mixture stirred for overnight at room temperature. After the reaction was complete, the volatiles were evaporated and $CH_2Cl_2$ (25 mL) added. The solution was washed with 1M NaOH (10 mL) followed by 1M HCl (10 mL). The organics were dried ($MgSO_4$) and evaporated. The residue was purified via column chromatography ($CH_2Cl_2$ to $CH_2Cl_2$15% EtOAc) to afford T-10 (573 mgs, 53% (over two steps).

Synthesis of Compound T-11

In a 250 mL round-bottomed flask was weighed T-1 (1.8 g, 10 mmol). Dry DCE (20 mL) was added followed by 2-bromoisopropylbenzene (2.0 g, 10 mmol, 1 equiv). Then $AlCl_3$ (133 mg, 1 mmol, 10 mol %) was added in portions. The resulting mixture was stirred under argon for 16 h. The mixture was cooled to room temperature, and then poured on ice-water (50 mL). The organic layer was separated and the aqueous layer was extracted with $Et_2O$ (2×20 mL). The organics were combined, dried ($MgSO_4$) and the solvent was evaporated. The residue was attempted to purify via column chromatography (hexanes) to afford the title compound as a mixture with starting material. The starting material was removed via distillation to afford the desired product as the residual pale yellow solid T-11 (260 mg, 9% yield).

Synthesis of Compound T-12

In a 50 mL round-bottomed flask T-11 (250 mg, 0.8 mmol) was dissolved in dry THF (5 mL) under argon. The mixture was cooled to −78° C. and n-BuLi (1.8 M, 0.54 mL, 1.2 equiv) added. The reaction was stirred for 30 mins at −78° C. and crushed dry ice was added. The mixture was warmed to room temperature, then quenched with 10 mL H2O. The THF was evaporated, then the reaction mixture was extracted with Et$_2$O (2×10 mL). The aqueous layer was acidified and extracted with EtOAc (2×20 mL). The organic layers were combined, dried (MgSO$_4$) and evaporated to afford the compound T-12 (97 mg, 44%) which was used without further purification.

Synthesis of Compound T-14

In a 50 mL round-bottomed flask 4-carboxy benzene acetic acid (950 mg, 5.3 mmol) was dissolved in MeOH (12 mL). Two drops of thionyl chloride were added and the mixture stirred at room temperature for 4 h. The solvent was evaporated, Et$_2$O (50 mL) was added and extracted with sat. NaHCO$_3$. The aqueous layer was acidified and extracted with ether (2×10 mL) and the aqueous layer was acidified with 2M HCl and extracted with ether (2×25 mL). The product T-14 (304 mg, 29%) was used without further purification.

Synthesis of Compound T-16

In a 50 mL round-bottomed flask T-14 (100 mg, 0.52 mmol) was dissolved in dry CH$_2$Cl$_2$ (3 mL) under argon. Added were oxalyl chloride (67 μL, 0.78 mmol 1.5 equiv) and one drop of DMF. The reaction was heated to 40° C. for 1 h. Then the solvents were evaporated to dryness and 2 mL of CH$_2$Cl$_2$ added. This solution was added dropwise to a solution of 1,1,4,4-tetramethyl-6-amino tetraline (105 mg, 0.52 mmol, 1 equiv) and Et$_3$N (0.22 mL, 1.56 mmol, 3 equiv) in CH$_2$Cl$_2$ (5 mL). The mixture was stirred for 5 h at room temperature, then EtOAc was added (30 mL), and the solution washed with 2M HCl (2×10 mL) and finally with 1M NaOH (10 mL). The organic layer was dried (MgSO$_4$) and evaporated. The residue was purified via column chromatography (CH$_2$Cl$_2$) to afford the title compound T-16 (167 mg, 85%) as a colorless solid.

Synthesis of Compound T-17

In a 50 mL round-bottomed flask T-16 (165 mg, 0.435 mmol) was dissolved in THF/H$_2$O (5/2 mL). LiOH (100 mg, 2.38 mmol, 5.5 equiv) was added and the mixture was stirred for at room temperature until TLC indicates reaction completion. THF was evaporated, aqueous layer was extracted with ether (2×10 mL) and the aqueous layer was acidified with 2M HCl and extracted with ether (2×25 mL). The organics were evaporated to afford the title compound T-17 (133 mg, 84%) as a colorless solid.

Synthesis of Compound T-18

In a 50 mL round-bottomed flask T-12 (102 mg, 0.37 mmol) was dissolved in dry CH$_2$Cl$_2$ (3 mL) under argon. Added were oxalyl chloride (50 μL, 0.55 mmol, 1.5 equiv) and one drop of DMF. The reaction was heated to 40° C. for 2 h. Then the solvents were evaporated to dryness and 2 mL CH$_2$Cl$_2$ added. This solution was added dropwise to a solution of 4-aminobenzene acetic acid methyl ester (75 mg, 0.44 mmol, 1.2 equiv) and Et$_3$N (0.16 mL, 1.11 mmol, 3 equiv) in CH$_2$Cl$_2$ (5 mL). The resulting solution was stirred for 5 h at room temperature. EtOAc (30 mL) was added, and the solution washed with 2M HCl (2×10 mL). The organic layer was dried (MgSO$_4$) and evaporated. The residue was purified via column chromatography (CH$_2$Cl$_2$+5% EtOAc) to afford the title compound T-18 (122 mg, 78%) as a colorless solid.

Synthesis of Compound T-19

In a 50 mL round-bottomed flask T-18 (115 mg, 0.27 mmol) was dissolved in THF/H$_2$O (3/2 mL). LiOH (50 mg, 1.19 mmol, 4.4 equiv) was added and the mixture was stirred for at room temperature until TLC indicates reaction completion. THF was evaporated, aqueous layer was extracted with ether (2×10 mL) and the aqueous layer was then acidified with 2M HCl and extracted with ether (2×25 mL). The organics were combined, dried (MgSO$_4$) and evaporated to afford the title compound T-19 (101 mg, 91%) as a tan solid.

Synthesis of Compound T-20

In a 50 mL round-bottomed flask 2-fluoro-4-nitrobenzene acetic acid (800 mg, 4.0 mmol) was dissolved in MeOH (10 mL). Catalytic thionyl chloride was added and the solution stirred at room temperature overnight. The solvent was evaporated, and the residue purified using column chromatography (pentane/Et$_2$O, 9/1 to 5/1) to afford the title compound T-20 (325 mg, 38%) as a colorless oil.

Synthesis of Compound T-21

In a 50 mL round-bottomed flask 20 (300 mg, 1.4 mmol) was dissolved in MeOH (10 mL) and Pd/C (10%, 75 mg) was added and the mixture hydrogenated with a hydrogen balloon overnight. The mixture was filtered, and evaporated to afford the title compound T-21 quantatively as a reddish oil which was used without further purification.

Synthesis of Compound T-22

In a 25 mL round-bottomed flask crude T-4 (315 mg, 1.1 mmol) was dissolved in CH$_2$Cl$_2$ (10 mL) under argon. T-21 (220 mg, 1.2 equiv, 1.3 mmol) dissolved in CH$_2$Cl$_2$ (5 mL) was added and the mixture was stirred for 1 h. Then pyridine (0.5 mL) was added and the mixture stirred for 72 h at room temperature. After the reaction is complete, the volatiles were evaporated, CH$_2$Cl$_2$ (25 mL) added and the solution wash with 1M NaOH (10 mL) followed by 1M HCl (10 mL). The organics were separated, dried (MgSO$_4$) and evaporated. The residue was purified via column chromatography (DCM to DCM/5% EtOAc) to afford T-22 (205 mgs, 44% (over two steps)).

Synthesis of Compound T-24

In a 50 mL round-bottomed flask phenyl methyl acetate (200 mg, 1.33 mmol) was added to 0.5 mL of chlorosulfonic acid at room temperature. The dark reaction mixture was stirred for 2 h at room temperature followed by 1 h at 45° C. The mixture was poured on ice-water, and extracted with DCM (2×20 mL). The organic layer was dried (MgSO$_4$) and evaporated to afford T-24 as a beige solid, which was used directly without further purification.

Synthesis of Compound T-25

In a 50 mL round-bottomed flask phenyl methyl acetate (200 mg, 1.33 mmol) was added to 0.5 mL of chlorosulfonic acid at room temperature. The dark reaction mixture was stirred for 2 h at room temperature followed by 1 h at 45° C. The mixture was poured on ice-water, and extracted with DCM (2×20 mL). The organic layer was dried ($MgSO_4$) and evaporated to afford T-24 as a beige solid, which was used directly without further purification.

T-24 was dissolved in 5 mL $CH_2Cl_2$. Added to this solution dropwise were a solution of 15 (150 mg, 0.75 mmol) and pyridine (0.5 mL) in $CH_2Cl_2$ (5 mL). The mixture was stirred overnight at room temperature. After the reaction is complete, the volatiles were evaporated and $CH_2Cl_2$ (25 mL) added and the solution washed with 1M NaOH (10 mL) followed by 1M HCl (10 mL). The organics were dried ($MgSO_4$) and evaporated. The residue is purified via column chromatography (DCM to DCM/2% $Et_2O$) to afford T-25 as a colorless oil (192 mgs, mixture of two isomeric compounds).

Synthesis of Compound T-26

In a 250 mL round-bottomed flask was weighed T-1 (1.8 g, 10 mmol). Dry DCE (20 mL) was added followed by isopropylbenzene (1.2 g, 10 mmol). Then $AlCl_3$ (133 mg, 1 mmol, 10 mol %) was added in portions. The resulting mixture was stirred under argon for 16 h. The mixture was cooled to room temperature, and then poured on ice-water (50 mL). The organic layer was separated and the aqueous layer was extracted with $Et_2O$ (2×20 mL). The organics were combined, dried ($MgSO_4$) and the solvent was evaporated. The residue was purified via column chromatography (pentane) to afford the title compound T-26 as a colorless oil (540 mg, 23% yield).

Synthesis of Compound T-27

T-26 was dissolved in 5 mL $CH_2Cl_2$. Added to this solution dropwise were a solution of aniline (150 mg, 0.75 mmol) and pyridine (0.5 mL) in $CH_2Cl_2$ (5 mL). Stir the mixture overnight at room temperature. After the reaction was complete, volatiles were evaporate and $CH_2Cl_2$ (25 mL) was added and washed with 1M NaOH (10 mL) followed by 1M HCl (10 mL). Dry ($MgSO_4$) and evaporate. The resulting residue was purified via column chromatography (DCM to DCM/2% $Et_2O$) to afford T-27 as a colorless oil (192 mgs, mixture of two isomeric compounds).

In a 50 mL round-bottomed flask T-25 (180 mg, 0.43 mmol, [mixture]) was dissolved in $THF/H_2O$ (3/1.5 mL). LiOH (61 mg, 1.45 mmol, 3.4 equiv) was added and the mixture was stirred for at room temperature until TLC indicates reaction completion. THF was evaporated and the aqueous layer was extracted with ether (2×10 mL). Then the aqueous layer was acidified with 2M HCl and extracted with ether (2×25 mL). The organics were combined, dried ($MgSO_4$) and evaporated to afford the title compound T-27, containing still impurities. The material was recrystallized three times from c-Hex/$Et_2O$ to afford pure T-27.

Synthesis of Compound T-28

In a 10 mL round-bottomed flask 1 mL of chlorosulfonic acid was added and cooled to 10° C. T-26 (230 mg, 1 mmol) was added and the mixture was left to warm to room temperature. The dark reaction mixture was stirred for 4 h and then poured on ice-water and extracted with DCM (2×20 mL). The organic layer was dried ($MgSO_4$) and evaporated to afford T-28 as a greenish solid, which was used directly without further purification.

Synthesis of Compound T-29

In a 50 mL round-bottomed flask crude T-28 (330 mg, 1 mmol) was dissolved in $CH_2Cl_2$ (10 mL) under argon. 4-Aminobenzene acetic acid methyl ester (250 mg, 1.5 equiv, 1.5 mmol) was added and the mixture was stirred for 1 h. Then pyridine (0.5 mL) was added and the mixture stirred for overnight at room temperature. After the reaction is complete, the volatiles were evaporated. $CH_2Cl_2$ (25 mL) was added and the mixture washed with 1M NaOH (10 mL) followed by 1M HCl (10 mL). The combined organics were dried ($MgSO_4$) and evaporated. The residue is purified via column chromatography ($CH_2Cl_2$ to $CH_2Cl_{2/5}$% $Et_2O$) to afford T-29 (231 mgs, 50% (over two steps)).

Synthesis of Compound T-31

In a 50 mL round-bottomed flask ethyl-4-nitrophenylacetate (1.0 g, 4.8 mmol) was dissolved in THF/DMF (5/1 mL). MeI (1.2 mL, 19.2 mmol, 4 equiv) was added and then the solution was heated to 50° C. A suspension of KOtBu in THF (1.6 g, 14.4 mmol, 3 equiv in 15 mL THF) was added and a deep purple color persists. The reaction was kept at this temperature for 1 h (color turns brown) and poured onto 2M HCl (10 mL). The mixture was extracted with $Et_2O$ (2×100 mL), dried ($MgSO_4$) and evaporated. The residue was dissolved in $CH_2Cl_2$ and passed through a short silica gel plug to afford the desired product T-31 as pale yellow oil (830 mg, 73%).

Synthesis of Compound T-31A

In a 50 mL round-bottomed flask ethyl-4-nitrophenylacetate (1.0 g, 4.8 mmol) was dissolved in THF/DMF (5/1 mL). EtI (1.5 mL, 19.2 mmol, 4 equiv) was added and then the solution was heated to 50° C. A suspension of KOtBu in THF (1.6 g, 14.4 mmol, 3 equiv in 15 mL THF) was added and a deep purple color persists. The reaction was kept at this temperature for 1 h (color turns brown) and poured onto 2M HCl (10 mL). The mixture was extracted with $Et_2O$ (2×100 mL), dried ($MgSO_4$) and evaporated. The residue was dissolved in $CH_2Cl_2$ and passed through a short silica gel plug to afford the desired product T-31 as pale yellow oil (912 mg, 72%).

Synthesis of Compound T-31C

In a 50 mL round-bottomed flask ethyl-4-nitrophenylacetate (0.5 g, 2.6 mmol) was dissolved in THF/DMF (10/1 mL). iPrI (1.0 mL, 10.3 mmol, 4 equiv) was added and then the solution was heated to 50° C. A suspension of KOtBu in THF (0.9 g, 7.7 mmol, 3 equiv in 10 mL THF) was added and a deep purple color persists. The reaction was kept at this temperature for 1 h (color turns brown) and poured onto 2M HCl (10 mL). The mixture was extracted with $Et_2O$ (2×100 mL), dried ($MgSO_4$) and evaporated. The residue was dissolved in $CH_2Cl_2$ and passed through a short silica gel plug to afford the desired product T-31C as pale yellow oil (413 mg, 68%).

Synthesis of Compound T-32

In a 50 mL round-bottomed flask T-31 (830 mg, 3.5 mmol) was dissolved in EtOH (10 mL) and Pd/C (10%, 150 mg) was added. The mixture was hydrogenated with a hydrogen balloon overnight. The mixture was filtered, and evaporated to afford the title compound T-32 quantatively as a colorless oil which was used without further purification.

Synthesis of Compound T-32A

In a 50 mL round-bottomed flask T-31A (912 mg, 3.5 mmol) was dissolved in EtOH (10 mL) and Pd/C (10%, 150 mg) was added. The mixture was hydrogenated with a hydrogen balloon overnight. The mixture was filtered, and evaporated to afford the title compound T-32A quantatively as a colorless oil which was used without further purification.

Synthesis of Compound T-32C

In a 50 mL round-bottomed flask T-31C (200 mg, 1.7 mmol) was dissolved in EtOH (5 mL) and Pd/C (5%, 50 mg) was added. The mixture was hydrogenated with a hydrogen balloon overnight. The mixture was filtered, and evaporated to afford the title compound T-32C quantatively as a colorless oil which was used without further purification.

Synthesis of Compound T-33

In a 250 mL round-bottomed flask was weighed T-1 (1.8 g, 10 mmol). Dry DCE (20 mL) was added followed by 2-bromo-1,3-dimethylbenzene (1.3 mL, 10 mmol, 1 equiv). Then $AlCl_3$ (266 mg, 2 mmol, 20 mol %) was added in portions. The resulting mixture was stirred under argon for 16 h. The mixture was cooled to room temperature, and then poured on ice-water (50 mL). The organic layer was separated and the aqueous layer was extracted with $Et_2O$ (2×20 mL). The organics were combined, dried (MgSO4) and the solvent was evaporated. The residue was purified via column chromatography (pentane) to afford the title compound T-33 as a colorless solid (440 mg, 15% yield).

Synthesis of Compound T-34

In a 50 mL round-bottomed flask 33 (810 mg, 3.76 mmol) was dissolved in dry THF (20 mL) under argon. The mixture was cooled to −78° C. and t-BuLi (1.5 M, 5.5 mL, 8.25 mmol, 2.2 equiv) was added. The reaction was stirred for 30 mins at −78° C. and crushed dry ice was added. The mixture was warmed to room temperature, and then quenched with 10 mL $H_2O$. The THF was evaporated, then extracted the reaction mixture with $Et_2O$ (2×10 mL). The aqueous layer was acidified, and extracted with EtOAc (2×20 mL). The organic layers were combined, dried ($MgSO_4$) and evaporated to afford the compound T-34 (610 mg, 90%) as a colorless solid which was used without further purification.

Synthesis of Compound T-35

In a 50 mL round-bottomed flask T-34 (210 mg, 1.0 mmol) was dissolved in dry $CH_2Cl_2$ (6 mL) under argon. Added were oxalyl chloride (130 µL, 1.5 mmol, 1.5 equiv) and one drop of DMF. The reaction was heated to 40° C. for 2 h. Then the solvents were evaporated to dryness and 3 mL $CH_2Cl_2$ was added. Added to this solution dropwise was a solution of 4-aminobenzene acetic acid methyl ester (200 mg, 1.2 mmol, 1.2 equiv) and $Et_3N$ (0.42 mL, 3.0 mmol, 3 equiv) in $CH_2Cl_2$ (10 mL). The reaction mixture was stirred for 16 h at room temperature. EtOAc (30 mL) was added, and then washed with 2M HCl (2×10 mL). The organic layer was dried ($MgSO_4$) and evaporated. The residue was purified via column chromatography (pentane/EtOAc 9/1 to 1/1) to afford the title compound T-35 (200 mg, 49%) as a colorless fluffy solid.

Synthesis of Compound T-36

In a 50 mL round-bottomed flask T-35 (200 mg, 0.49 mmol) was dissolved in $THF/H_2O$ (5/2.5 mL). LiOH (62 mg, 1.47 mmol, 3.0 equiv) was added and the mixture was stirred for at room temperature until TLC indicates reaction completion. THF was evaporated, aqueous layer was extracted with ether (2×10 mL) and finally the aqueous layer was acidified with 2M HCl and extracted with EtOAc (2×25 mL). The organics were combined, dried ($MgSO_4$) and evaporated to afford the title compound T-36 (180 mg, 93%) as a colorless puffy solid. The compound was further triturated with $Et_2O$ to increase the purity.

Synthesis of Compound T-37

In a 50 mL round-bottomed flask crude T-9 (225 mg, 0.75 mmol) was dissolved in $CH_2Cl_2$ (10 mL) under argon. T-32 (185 mg, 0.9 mmol, 1.2 equiv) was added and the mixture was stirred for 1 h. Then pyridine (0.5 mL) was added and the mixture stirred for overnight at room temperature. After the reaction was complete, the volatiles were evaporated and $CH_2Cl_2$ (25 mL) added. The mixture was washed with 1M NaOH (10 mL) followed by 1M HCl (10 mL). The organics were dried ($MgSO_4$) and evaporated. The residue is purified via column chromatography ($CH_2Cl_2$ to $CH_2Cl_{2/5}$% EtOAc) to afford T-37 (184 mgs, 52% (over two steps)).

Synthesis of Compound T-37A

In a 50 mL round-bottomed flask crude T-9 (225 mg, 0.79 mmol) was dissolved in $CH_2Cl_2$ (10 mL) under argon. T-32A (222 mg, 0.9 mmol, 1.2 equiv) was added and the mixture was stirred for 1 h. Then pyridine (0.5 mL) was added and the mixture stirred for overnight at room temperature. After the reaction was complete, the volatiles were evaporated and $CH_2Cl_2$ (25 mL) added. The mixture was washed with 1M NaOH (10 mL) followed by 1M HCl (10 mL). The organics were dried ($MgSO_4$) and evaporated. The residue is purified via column chromatography ($CH_2Cl_2$ to $CH_2Cl_2$/5% EtOAc) to afford T-37A (200 mg, 54% (over two steps)).

Synthesis of Compound T-37B

In a 50 mL round-bottomed flask crude T-9 (230 mg, 0.76 mmol) was dissolved in $CH_2Cl_2$ (10 mL) under argon. T-32A (202 mg, 0.9 mmol, 1.2 equiv) was added and the mixture was stirred for 1 h. Then pyridine (0.5 mL) was added and the mixture stirred for overnight at room temperature. After the reaction was complete, the volatiles were evaporated and $CH_2Cl_2$ (25 mL) added. The mixture was washed with 1M NaOH (10 mL) followed by 1M HCl (10 mL). The organics were dried ($MgSO_4$) and evaporated. The residue is purified via column chromatography ($CH_2Cl_2$ to $CH_2Cl_2$/5% EtOAc) to afford T-37A (161 mg, 50% (over two steps)).

Synthesis of Compound T-37C

In a 50 mL round-bottomed flask crude T-9 (100 mg, 0.3 mmol) was dissolved in $CH_2Cl_2$ (10 mL) under argon. T-32C (102 mg, 0.5 mmol, 1.5 equiv) was added and the mixture was stirred for 1 h. Then pyridine (0.5 mL) was added and the mixture stirred for overnight at room temperature. After the reaction was complete, the volatiles were evaporated and $CH_2Cl_2$ (25 mL) added. The mixture was washed with 1M NaOH (10 mL) followed by 1M HCl (10 mL). The organics were dried ($MgSO_4$) and evaporated. The residue is purified via column chromatography ($CH_2Cl_2$ to $CH_2Cl_2$/5% EtOAc) to afford T-37C (81 mgs, 52% (over two steps)).

Synthesis of Compound T-38

In a 50 mL round-bottomed flask crude T-9 (225 mg, 0.75 mmol) was dissolved in $CH_2Cl_2$ (10 mL) under argon. Methyl-4-aminobenzoate (136 mg, 1.2 equiv, 0.9 mmol) was added and the mixture was stirred for 1 h. Then pyridine (0.5 mL) was added and the mixture stirred for overnight at room temperature. After the reaction was complete, the volatiles were evaporated and $CH_2Cl_2$ (25 mL) added. The mixture was washed with 1M NaOH (10 mL) followed by 1M HCl (10 mL). The organic layer was dried ($MgSO_4$) and evaporated. The residue was purified via column chromatography (DCM to DCM/5% EtOAc) to afford T-38 (118 mgs, 38% (over two steps)).

Synthesis of Compound T-40

In a 50 mL round-bottomed flask T-33 (762 mg, 2.6 mmol) was dissolved in MeOH/EtOAc/H2O (10/10/0.5 mL) and KOH (290 mg, 5.2 mmol, 2 equiv) and Pd/C (10%, 150 mg) was added and the mixture hydrogenated with a hydrogen balloon overnight. The mixture was filtered through Celite and followed by a silica plug. The residue evaporated to afford the title compound T-40 (480 mg, 86%) as a colorless oil which was used without further purification.

Synthesis of Compound T-41

In a 50 mL round-bottomed flask ethyl-4-nitrophenylacetate (2.09 g, 10 mmol) was dissolved in DMF (15 mL). Added was NaH (60%, 840 mg, 21 mmol, 2.1 equiv) with ice-cooling, and then the solution was warmed to room temperature and stirred for 1 h. The mixture was cooled back to 0° C. and dibromoethane (1.72 mL, 20 mmol, 2.0 equiv) was added. The reaction was stirred at the same temperature for 30 mins, and then at room temperature for 1 h. The mixture was then carefully quenched with $H_2O$ and extracted with $CH_2Cl_2$ (2×30 mL). The combined organics were dried ($MgSO_4$) and evaporated. The residue was purified via column chromatography (pentane/$Et_2O$) to afford the title compound T-41 as a colorless solid (632 mg, 27%).

Synthesis of Compound T-42

In a 50 mL round-bottomed flask T-41 (620 mg, 2.6 mmol) was dissolved in EtOH (10 mL) and EtOAc (2 mL). Pd/C (10%, 100 mg) was added and the mixture hydrogenated with a hydrogen balloon overnight at room temperature. The mixture was filtered, and evaporated to afford the title compound T-42 quantatively as a colorless oil which was used without further purification.

Synthesis of Compound T-43

In a 50 mL round-bottomed flask crude 9 (180 mg, 0.59 mmol) was dissolved in $CH_2Cl_2$ (5 mL) under argon. T-42 (180 mg, 1.5 equiv, 0.88 mmol) was added and the mixture was stirred for 1 h. Then pyridine (0.5 mL) was added and the mixture stirred for overnight at room temperature. After the reaction was complete, the volatiles were evaporated and $CH_2Cl_2$ (25 mL) added. The mixture was washed with 1M NaOH (10 mL) followed by 1M HCl (10 mL). The organics were dried ($MgSO_4$) and evaporated. The residue was purified via column chromatography ($CH_2Cl_2$ to $CH_2Cl_2$/5% $Et_2O$) to afford T-43 (67 mgs, 24% (over two steps)).

Synthesis of Compound 17A

Compound 17A was synthesized analogously to compound T-37 from unpurified T-4 (1 equiv) dissolved in $CH_2Cl_2$ (10 mL/mmol). SS-101 (1.2 equiv) was added and the mixture was stirred for 1 h. Then pyridine (0.7 mL/mmol) was added and the mixture stirred for overnight at room temperature. After the reaction was complete and a standard workup the residue was purified via column chromatography to afford the title compound 17A.

Synthesis of Compound 19B

Compound 19B was synthesized analogously to compound T-37 from unpurified T-9 (1 equiv) dissolved in $CH_2Cl_2$ (10 mL/mmol). Compound T-32C (1.2 equiv) was added and the mixture was stirred for 1 h. Then pyridine (0.7 mL/mmol) was added and the mixture stirred for overnight at room temperature. After the reaction was complete and a standard workup the residue was purified via column chromatography to afford the title compound 19B.

Synthesis of Compound SS-100

Compound SS-100 was synthesized analogously to compound T-31 except that ethyl iodide (EtI) was used instead of methyl iodide.

Synthesis of Compound SS-101

In a 50 mL round-bottomed flask compound SS-100 was dissolved in EtOH (3 mL/mmol) and Pd/C (10%, 50 mg/mmol) was added. The mixture was hydrogenated with a hydrogen balloon overnight. The mixture was filtered, and evaporated to afford the title compound SS-101 as a colorless oil which was used without further purification.

Synthesis of Compound SS-200

The title compound was synthesized analogously to compound T-31 except that isopropyl iodide (iPrI) was used instead of methyl iodide.

Synthesis of Compound SS-201

In a 50 mL round-bottomed flask SS-200 was dissolved in EtOH (3 mL/mmol) and Pd/C (10%, 50 mg/mmol) was added. The mixture was hydrogenated with a hydrogen balloon overnight. The mixture was filtered, and evaporated to afford the title compound SS-201 quantatively as a colorless oil which was used without further purification.

Example 1B. Synthesis of Compounds of Formula (1)

Synthetic descriptions of representative examples of compounds of Formula (1) have been provided here. Persons with skill in the art of the invention will recognize that structurally related compounds can be prepared in a similar way as the steps described below.

Synthesis of Compound 4 (a.k.a., T-7)

In a 50 mL round-bottomed flask T-6 (400 mg, 0.97 mmol) was dissolved in THF/H$_2$O (10/5 mL). LiOH (204 mg, 4.85 mmol, 5 equiv) was added and the mixture was stirred for at room temperature until TLC indicates reaction completion. THF was evaporated, aqueous layer was extracted with ether (2×10 mL) and the aqueous layer acidified with 2M HCl and extracted with ether (2×25 mL). The organics were evaporated to afford the title compound 4 (a.k.a. T-7) (309 mg, 80%). This was recrystallized from c-Hex/Et$_2$O to increase the purity.

$^1$H NMR δ (CDCl$_3$, 400 MHz): 1.12 (s, 6H), 1.24 (s, 6H), 1.60-1.65 (m, 4H), 3.57 (s, 2H), 6.7 (br s, 1H), 7.04 (d, J=8.8 Hz, 2H), 7.16 (d, J=8.4 Hz, 2H), 7.35 (d, J=8.2 Hz, 1H), 7.50 (dd, J=2.1, 8.4 Hz, 1H), 7.58 (d, J=2.0 Hz, 1H) ppm.

Molecular Weight: 401.52, Formula: C$_{22}$H$_{27}$NO$_4$S. Purity (HPLC): >96% (HPLC details: 50:50 MeOH:MeCN, Agilent Zorbax sb-aq 5 μm; 254 nm; 0.5 ml/min), Melting point: 159-160° C.

$^1$H NMR (CDCl$_3$, 400 MHz): 1.12 (s, 6H), 1.24 (s, 6H), 1.60-1.65 (m, 4H), 3.57 (s, 2H), 6.7 (br s, 1H), 7.04 (d, J=8.8 Hz, 2H), 7.16 (d, J=8.4 Hz, 2H), 7.35 (d, J=8.2 Hz, 1H), 7.50 (dd, J=2.1, 8.4 Hz, 1H), 7.58 (d, J=2.0 Hz, 1H) ppm.

Synthesis of Compound 7 (a.k.a. T-13)

In a 50 mL round-bottomed flask T-10 (350 mg, 0.82 mmol) was dissolved in THF/H$_2$O (6/3 mL). LiOH (100 mg, 2.38 mmol, 2.9 equiv) was added and the mixture was stirred for at room temperature until TLC indicates reaction completion. THF was evaporated, the aqueous layer was extracted with ether (2×10 mL) and acidified with 2M HCl and extracted with ether (2×25 mL). The organics were evaporated to afford the title compound 7 (a.k.a. T-13) (220 mg, 80%).

Molecular Weight: 415.55, Formula: C23H29NSO4, Purity (HPLC): >95% (HPLC details: 50:50 MeOH:MeCN, Agilent Zorbax sb-aq 5 μm; 254 nm; 0.5 ml/min), Melting point: 188-190° C.

$^1$H-NMR (400 MHz, DMSO-de): 1.14 (s, 6H), 1.20 (s, 6H), 1.59 (s, 4H), 2.50 (s, 3H, overlaps with the DMSO signal), 3.41 (s, 2H), 7.02 (d, J=8.6 Hz, 2H), 7.08 (d, J=8.6 Hz, 2H), 7.28 (s, 1H), 7.72 (s, 1H), 10.29 (br s, 1H), 12.22 (s, 1H) ppm.

$^{13}$C-NMR (100 MHz, DMSO-d): 32.0, 32.2, 34.6, 34.9, 35.0, 35.1, 119.4, 128.2, 130.9, 131.5, 134.0, 136.1, 137.4, 143.2, 150.3, 173.5 ppm.

Synthesis of Compound 9 (a.k.a. T-23)

In a 50 mL round-bottomed flask T-22 (150 mg, 0.35 mmol) was dissolved in THF/H$_2$O (2/1 mL). LiOH (44 mg, 1.05 mmol, 3 equiv) was added and the mixture was stirred for at room temperature until TLC indicates reaction completion. THF was evaporated, aqueous layer was extracted with ether (2×10 mL) and then the aqueous layer was acidified with 2M HCl and extracted with ether (2×25 mL). The organics were combined, dried (MgSO$_4$) and evaporated to afford the title compound 9 (a.k.a. T-23) (138 mg, 94%) as a beige solid.

Molecular Weight: 419.51, Formula: C$_{22}$H$_{26}$FNSO$_4$. Purity (HPLC): >98% (HPLC details: 50:50 MeOH:MeCN, Agilent Zorbax sb-aq 5 μm; 254 nm; 0.5 ml/min), Melting point: >157.5-159.0° C.

$^1$H-NMR (400 MHz, DMSO-de): 1.18 (s, 6H), 1.22 (s, 6H), 1.62 (s, 4H), 3.48 (s, 2H), 6.86-6.92 (m, 2H), 7.19 (t, J=8.3 Hz, 1H), 7.48-7.54 (m, 2H), 7.68 (d, J=1.6 Hz, 1H), 10.41 (s, 1H), 12.38 (s, 1H) ppm.

$^{13}$C-NMR (100 MHz, DMSO-de): 32.1, 32.2, 34.5, 34.8, 34.9, 35.1, 35.3, 107.1 (d, J=26.3 Hz), 116.1 (d, J=2.5 Hz), 118.5 (d, J=16 Hz), 124.4, 125.7, 128.6, 133.3 (d, J=5.8 Hz), 137.5, 139.3 (d, J=10.6 Hz), 146.5, 150.9, 161.4 (d, J=244.3 Hz) 172.5 ppm.

Synthesis of Compound 11 (a.k.a. T-30)

In a 50 mL round-bottomed flask T-29 (140 mg, 0.3 mmol) was dissolved in THF/H2O (3/1.5 mL). LiOH (45 mg, 1.07 mmol, 3.5 equiv) was added and the mixture was stirred at room temperature until TLC indicates reaction completion. THF was evaporated, aqueous layer was extracted with ether (2×10 mL) and finally the aqueous layer was acidified with 2M HCl and extracted with ether (2×25 mL). The organics were combined, dried (MgSO$_4$) and evaporated to afford the title compound 30 (121 mg, 93%) as a tan solid. HPLC indicated only 94% purity so the material was further purified via column chromatography using pentane/EtOAc 1/1 to EtOAc to afford the product compound 11 (a.k.a. T-30), 76 mgs, of 98% purity.

Molecular Weight: 443.21, Formula: C$_{25}$H$_{33}$NSO$_4$, Purity (HPLC): >98% (HPLC Details: 50:50 MeOH:MeCN, Agilent Zorbax sb-aq 5 μm; 254 nm; 0.5 mL/min), Melting point: 208-211° C.

$^1$H-NMR (400 MHz, DMSO-de): 1.15 (m, 9H), 1.18 (s, 3H), 1.22 (s, 6H), 1.60 (s, 4H), 3.42 (s, 2H), 3.81 (sept, J=6.8 Hz, 1H), 7.04 (d, J=8.6 Hz, 2H), 7.09 (d, J=8.6 Hz, 2H), 7.42 (s, 1H), 7.73 (s, 1H), 10.37 (s, 1H), 12.22 (br s, 1H) ppm.

$^{13}$C-NMR (100 MHz, DMSO-de): 24.8, 29.0, 32.2, 34.6, 34.9, 35.1, 119.1, 126.8, 127.8, 130.7, 130.9, 135.4, 137.7, 143.0, 145.4, 150.6, 173.5 ppm.

Synthesis of Compound 12 (a.k.a. T-39)

In a 50 mL round-bottomed flask T-37 (184 mg, 0.4 mmol) was dissolved in MeOH/H$_2$O (5/2.5 mL). KOH (150 mg, 2.6 mmol, 6.5 equiv) was added and the mixture was heated at 50° C. overnight. Solvent was evaporated, aqueous layer was extracted with ether (2×10 mL) and the aqueous layer was acidified with 2M HCl and extracted with EtOAc (2×25 mL). The organics were evaporated to afford the title compound 12 (a.k.a. T-39) (46 mg, 27%) as an orange solid. The compound was further recrystallized from MeCN to increase the purity.

Molecular Weight: 443.60, Formula: C$_{25}$H$_{33}$NO$_4$S, Purity (HPLC): >98% (HPLC details: 50:50 MeOH:MeCN, Agilent Zorbax sb-aq 5 μm; 254 nm; 0.5 mL/min), Melting point >220° C.

$^1$H NMR (DMSO-de, 400 MHz): 1.12 (s, 6H), 1.20 (s, 6H), 1.37 (s, 6H), 1.59 (br s, 4H), 2.51 (s, 3H), 7.04 (d, J=8.8 Hz, 2H), 7.18 (d, J=8.7 Hz, 2H), 7.29 (s, 1H), 7.67 (s, 1H), 10.28 (s, 1H), 12.19 (br s, 1H) ppm.

Synthesis of Compound 14

Compound 14A was synthesized analogously to compound T-38 using crude T-4 (1 equiv) in CH$_2$Cl$_2$ (10 mL/mmol). Methyl-4-aminobenzoate (1.2 equiv) was added and the mixture was stirred for 1 h. Then pyridine (0.7 mL/mmol) was added and the mixture stirred for overnight at room temperature. A standard workup and purification via column chromatography afforded the title compound.

Compound 14 (a.k.a. T-44) was synthesized using 14A (1 equiv) in Et$_2$O/THF/H$_2$O (20/4/3 mL/mmol) and KOt-Bu (8.0 equiv). After a standard workup and purification via column chromatography the title compound was obtained.

Synthesis of Compound 13

In a 50 mL round-bottomed flask T-43 (200 mg, 0.43 mmol) was dissolved in MeOH/H$_2$O (5/2.5 mL). KOH (120 mg, 2.1 mmol, 5.0 equiv) was added and the mixture was heated at 50° C. overnight. Solvent was evaporated, aqueous layer was extracted with ether (2×10 mL) and the aqueous layer was acidified with 2M HCl and extracted with EtOAc (2×25 mL). The organics were evaporated to afford the title compound 13 (a.k.a. T-45) (145 mg, 77%) as a colorless solid.

Synthesis of Compound 17

Compound 17 was synthesized analogously to compound T-47 from T-37A (1 equiv) using MeOH/H$_2$O (10/5 mL/mmol) and KOH (5.0 equiv). After a standard workup and evaporation of the organics compound 17 was obtained, as a colorless solid. Characterization by NMR provided spectra that was as expected.

Synthesis of Compound 18

In a 50 mL round-bottomed flask T-17A (200 mg, 0.41 mmol) was dissolved in THF (5 mL). LiOH.H$_2$O (52 mg, 1.2 mmol, 3.0 equiv) was added and the mixture was stirred at room temperature for 18 h. The reaction was quenched with H$_2$O, solvent was evaporated, aqueous layer was extracted with ether (2×10 mL) and the aqueous layer was acidified with 2M HCl and extracted with EtOAc (2×25 mL). The organics were evaporated to afford the title compound 18 (146 mg, 75%) as a colorless solid. Characterization by NMR provided spectra that was as expected.

Synthesis of Compound 19

In a 50 mL round-bottomed flask compound 19B (200 mg, 0.42 mmol) was dissolved in THF (5 mL). LiOH.H$_2$O (54 mg, 1.3 mmol, 3.0 equiv) was added and the mixture was stirred at room temperature for 18 h. The reaction was quenched with H$_2$O, solvent was evaporated, aqueous layer was extracted with ether (2×10 mL) and the aqueous layer was acidified with 2M HCl and extracted with EtOAc (2×25 mL). The organics were evaporated to afford the title compound 19 (138 mg, 71%) as a colorless solid.

Compound 19 was also synthesized analogously to compound T-47 from compound 19B (1 equiv) using MeOH/H$_2$O (10/5 mL/mmol) and KOH (5.0 equiv). After a standard workup and evaporation of the organics the title compound 19 was obtained. Characterization by NMR provided spectra that was as expected.

Synthesis of Compound 21

The synthetic scheme is presented below.

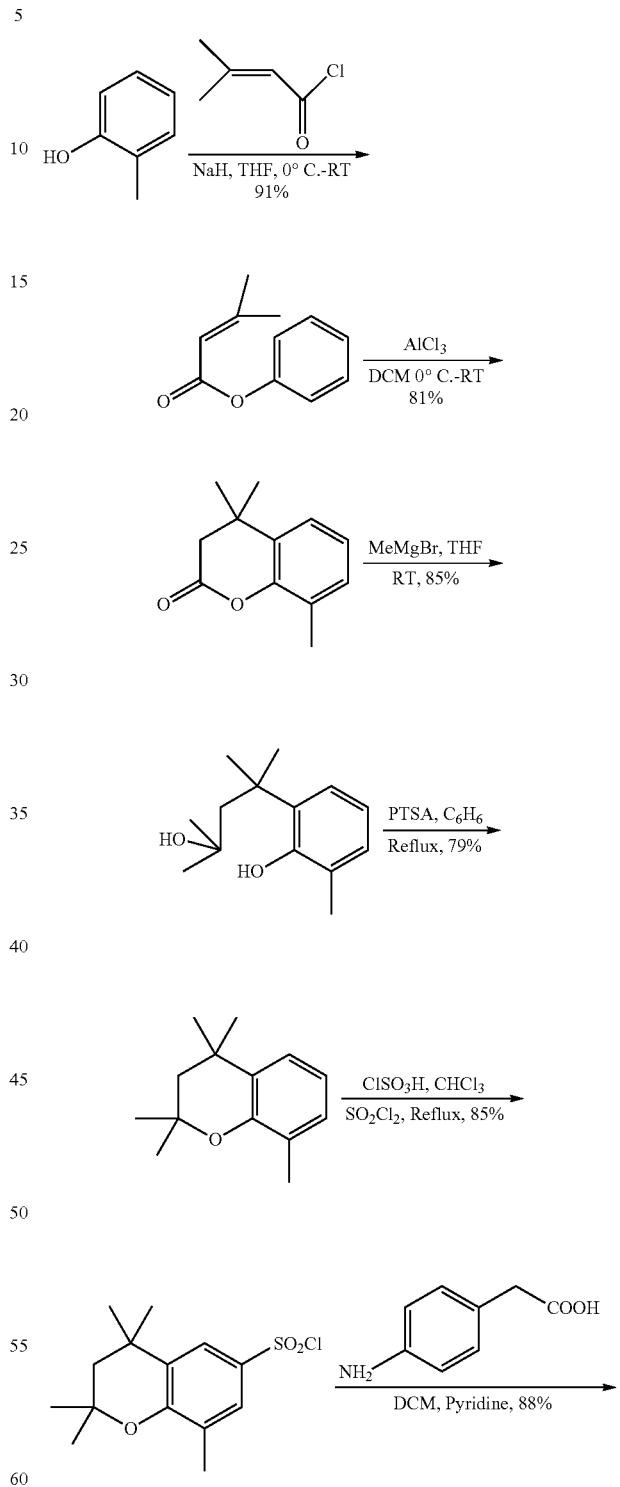

Compound 21

Molecular Weight: 417.55, Formula: $C_{22}H_{27}NO_5S$.

$^1$H-NMR (CDCl$_3$): 1.17 (s, 6H), 1.31 (s, 5H), 1.77 (s, 2H), 2.13 (s, 3H), 3.56 (s, 2H), 6.51 (s, 1H), 7.00 (d, 2H), 7.14 (d, 2H), 7.36 (d, 1H), 7.40 (d, 1H) ppm.

Example 2. Retinoid Activity Assays

This retinoid activity assay measures the ability of test compounds to induce expression of a transiently transfected RA sensitive reporter construct. In this assay, MCF-7 cells are transfected with a construct comprising an upstream promoter of the CYP26A1 gene containing 2 RA response elements driving expression of firefly luciferase (pCYP26A1-luc). Since CYP26A1 is highly inducible by RA in these cells, this construct serves as a sensitive reporter of retinoid-like transcriptional activity.

MCF-7 cells were maintained in RPMI-1640 medium containing 10% FBS. Exponentially growing cells were harvested by incubation in trypsin. Cells were then collected and plated in 24-well plates at 50,000 cells/well. Once cells reached 80-90% confluence (e.g., the next day), cells were transfected with two plasmids. The first plasmid was CYP26A1-luc construct (375 ng). The second plasmid was a control plasmid comprising the *Renilla* luciferase gene driven by constitutive thymidine kinase promoter (pRL-tk) (25 ng). Transfection was performed using FuGene 6 transfection reagent (Promega) with a 1:3 ratio of DNA:FuGene. 24 hours after transfection, cells were treated with test compounds diluted in DMSO in triplicate at 0.1, 1 and 10 µM final concentrations. As a positive control for reporter activation, cells were also treated with RA diluted in DMSO at the same concentrations listed above. DMSO treatment alone served as a negative control. After 24 hours of treatment, cells were harvested in passive lysis buffer (Promega) and luciferase activity in cell lysates were read using a luminometer. Data are expressed as the activity of firefly luciferase relative to *Renilla* luciferase (see Table 3). For CYP26A1 inhibitor compounds, no activation of the reporter was detected, while the related retinoid-like compound induces luciferase expression.

Figure 2:
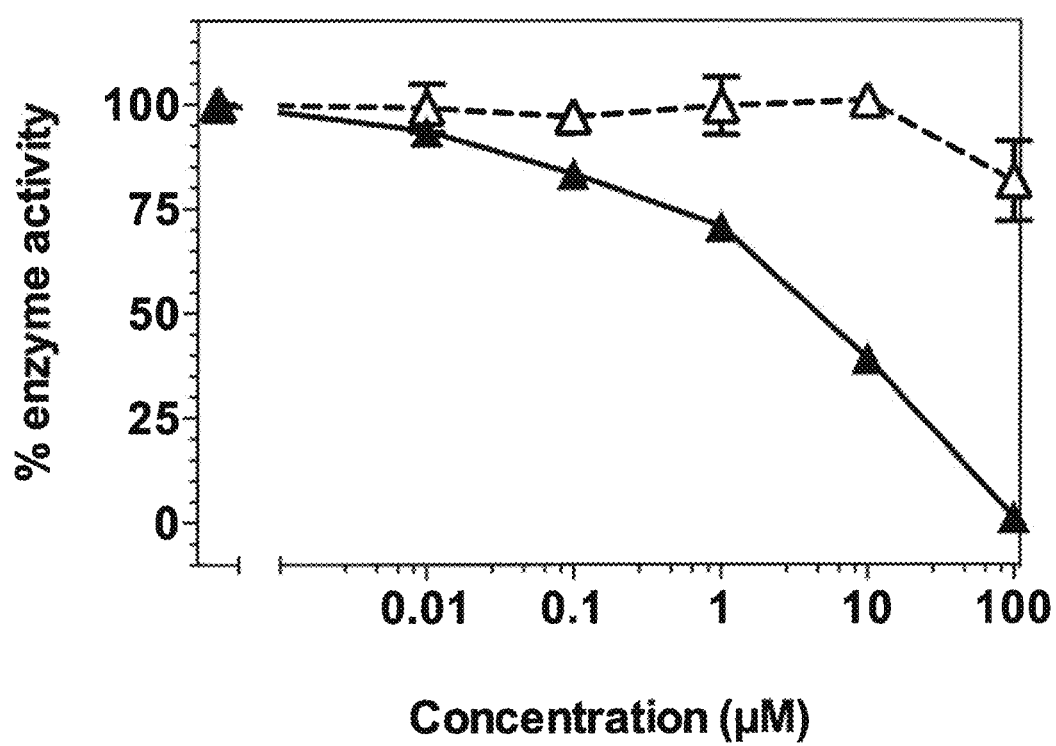
FIG. 2 shows a plot of activity of CYP26B1 enzyme in the presence of increasing concentration of compound 12 (Δ) versus ketoconazole (▲).

Additionally, for some compounds of particular interest, a second assay is performed to measure expression of endogenous RA target genes after treatment with test compounds in MCF-7 cells. Exponentially growing MCF-7 cells were treated with trypsin, collected and plated into 6-well culture dishes at 300,000 cells per well. Once cells reached confluency, they were treated with test compounds diluted in DMSO to a final concentration of 1 µM. As a positive control, cells were also treated with RA at 1 µM final concentration. After 24 hours of treatment, RNA was harvested using TRI reagent (available from Sigma-Aldrich, Oakville, Canada). cDNA was synthesized from 2 µg of total RNA using Superscript III cDNA synthesis kit with random priming (kit available from Life Technologies, Burlington, ON, Canada). Analysis of expression of a RA inducible CYP26A1 gene was quantified by qPCR normalized against expression of PMM2 with Sybr Select Master Mix (Life Technologies) and gene specific primers in a two-step thermal cycling reaction. Data is shown in Table 2 for select compounds of interest. Importantly, compounds that have inhibitory activity towards CYP26A1 did not significantly induce expression of RA target genes when given alone, indicating a lack of retinoid-like activity. See FIGS. 1 and 2 for graphs of retinoid activity.

Example 3. Enhancement of RA Activity Assay

An RA activity assay was used to measure the ability of compounds that inhibit CYP26A1 to enhance activity of RA, for example, by limiting its catabolism. This assay measured expression of endogenous RA target genes in MCF-7 cells that have been treated with RA and a compound of interest. A compound that inhibits CYP26 activity will have the effect of prolonging the induction of RA target genes in response to RA.

Figure 5:
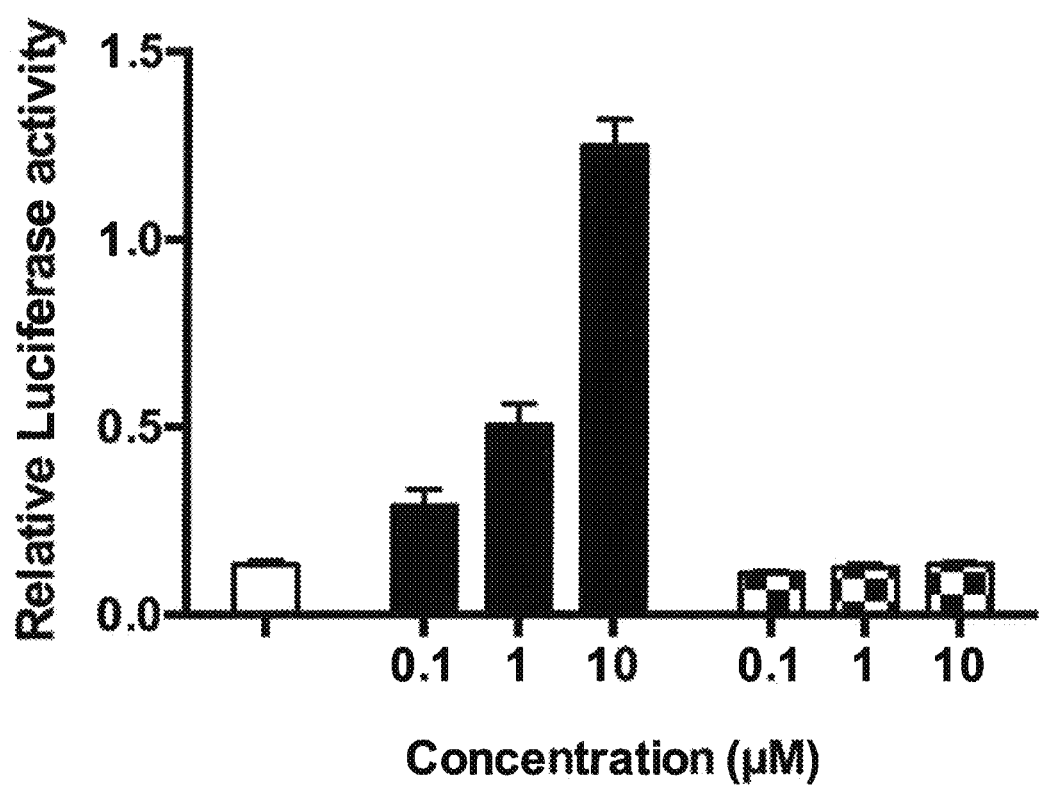
FIG. 5 shows a bar graph of agonist activity assessed by induction of a RA-sensitive luciferase reporter in MCF-7 cells, wherein MCF-7 cells were transfected with a Cyp26a1-promoter-luciferase plasmid along with a control *Renilla* luciferase plasmid for 24 hours prior to treatment with vehicle (DMSO), or increasing concentration of RA (black bars) or compound 14 (checkered bars). Luciferase activity was measured 24 hours later, and expressed as the relative activity of the Cyp26a1-promoter-luciferase/*Renillia* luciferase.

Exponentially growing MCF-7 cells were treated with trypsin, collected and plated into 6-well culture dishes at 300,000 cells per well. Once cells had reached confluency, they were treated with CYP26 inhibitor test compounds or with ketoconazole (a non-selective CYP inhibitor) at a final concentration of 1 µM, or an equal volume of DMSO as a control. RA was also added at a final concentration of 1 µM. RNA was harvested using Trizol reagent after 24, 48, and 72 hours of treatment. cDNA was synthesized from 2 µg of total RNA using Superscript III cDNA synthesis kit with random priming (available from Life Technologies, Burlington, ON, Canada). Analysis of expression of the RA inducible CYP26A1 gene was quantified by qPCR normalized against expression of PMM2 with Sybr Select Master Mix (Life Technologies) and gene specific primers in a two-step thermal cycling reaction. Data is provided for a CYP26A1 selective inhibitor, which enhances the induction of CYP26A1. See FIGS. 3 to 5 for GGP12 enhancement of RA signaling in MCF-7 cells.

Example 4. Cell-Based Inhibitor Assay

CYP26A1 or CYP26B1 stably transfected HeLa cells were maintained in Minimum Essential Medium (MEM) containing 10% fetal bovine serum (FBS) and 100 µg/mL hygromycin. Exponentially growing cells were harvested by incubation in trypsin. Cells were then collected and re-plated in 48-well culture plates at $5\times10^5$ cells in 0.2 mL of culture medium containing 0.05 µCi [H]-RA in the presence or absence of increasing concentrations of a test compound. The test compounds were diluted in dimethyl sulfoxide (DMSO) and then added in duplicate to wells at 0.01, 0.1, 1, 10 and 100 µM final concentration. As a positive control for inhibition of RA metabolism, cells were also incubated with ketoconazole at the same concentrations as above. Cells were incubated for 3 hours at 37° C. Retinoids were then extracted using the procedure of Bligh, et al., (1959), Canadian Journal of Biochemistry 37, 911-917, which was modified by using dichloromethane instead of chloroform. Each sample's water soluble radioactivity level was quantified using a β-scintillation counter (using Ecolume scintillation fluid, available from MP Biomedicals of Solon, Ohio, USA). $IC_{50}$ values represented the concentration of inhibitor required to inhibit all trans-RA metabolism by 50%, and were derived from log transformed data. $IC_{50}$ values obtained in this assay for several compounds are listed in Table 2.

It will be understood by those skilled in the art that this description is made with reference to certain preferred embodiments and that it is possible to make other embodiments employing the principles of the invention which fall within its spirit and scope as defined by the claims.

TABLE 1
Compound numbers, names, and structural formulae of compounds described herein
| Compound Number | Compound Name | Structural Formula |
|---|---|---|
|  | Liarozole | 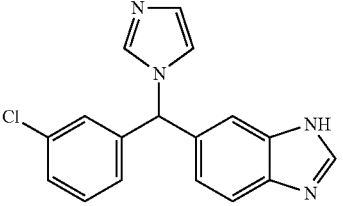 [SMILES: Clc1cccc(C(c2ccc3nc[nH]c3c2)n2ccnc2)c1] |
|  | Ketoconazole | 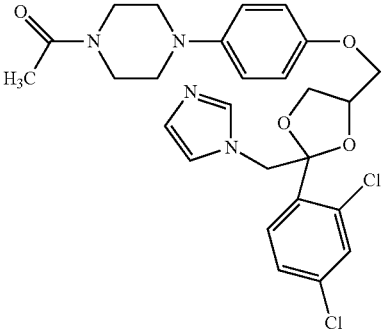 [SMILES: CC(=O)N1CCN(c2ccc(OCC3COC(Cn4ccnc4)(c4ccc(Cl)cc4Cl)O3)cc2)CC1] |
|  | R116010 | 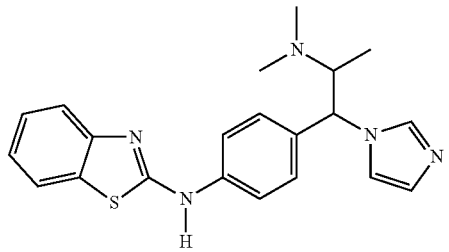 [SMILES: CC(C(c1ccc(Nc2nc3ccccc3s2)cc1)n1ccnc1)N(C)C] |
| T-1 |  | 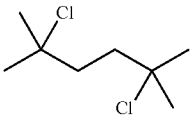 |
| T-2 |  | 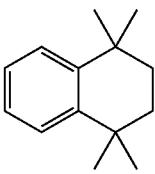 |
| T-3 |  | 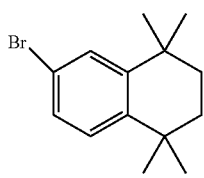 |
| T-4 |  | 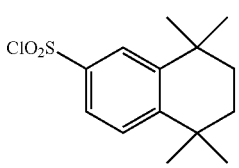 [SMILES: CC1(C)CCC(C)(C)c2cc(S(=O)(=O)Cl)ccc21] |

TABLE 1-continued

Compound numbers, names, and structural formulae of compounds described herein

| Compound Number | Compound Name | Structural Formula |
|---|---|---|
| T-5 | | |
| T-6 | | |
| T-7 | | |
| T-9 | | |
| T-10 | | |
| T-11 | | |
| T-12 | | |
| T-13 a.k.a 7 | | |

TABLE 1-continued

Compound numbers, names, and structural formulae of compounds described herein

| Compound Number | Compound Name | Structural Formula |
|---|---|---|
| T-14 | | 4-(methoxycarbonylmethyl)benzoic acid (HO₂C–C₆H₄–CH₂–CO₂Me) |
| T-16 | | N-(5,5,8,8-tetramethyl-5,6,7,8-tetrahydronaphthalen-2-yl)-4-(methoxycarbonylmethyl)benzamide |
| T-17 | | N-(5,5,8,8-tetramethyl-5,6,7,8-tetrahydronaphthalen-2-yl)-4-(carboxymethyl)benzamide |
| T-18 | | 3-isopropyl-5,5,8,8-tetramethyl-5,6,7,8-tetrahydronaphthalene-2-carboxylic acid [4-(methoxycarbonylmethyl)phenyl]amide |
| T-19 | | 3-isopropyl-5,5,8,8-tetramethyl-5,6,7,8-tetrahydronaphthalene-2-carboxylic acid [4-(carboxymethyl)phenyl]amide |
| T-20 | | methyl 2-(2-fluoro-4-nitrophenyl)acetate |
| T-21 | | methyl 2-(4-amino-2-fluorophenyl)acetate |

TABLE 1-continued

Compound numbers, names, and structural formulae of compounds described herein

| Compound Number | Compound Name | Structural Formula |
|---|---|---|
| T-22 | | |
| T-23 | | |
| T-24 | | |
| T-25 | | |
| T-26 | | |
| T-27 | | |
| T-28 | | |
| T-29 | | |

TABLE 1-continued

Compound numbers, names, and structural formulae of compounds described herein

| Compound Number | Compound Name | Structural Formula |
|---|---|---|
| T-30 | | |
| T-31 | | |
| T-31A | | |
| T-31C | | |
| T-32 | | |
| T-32A | | |
| T-33 | | |
| T-32C | | |

TABLE 1-continued

Compound numbers, names, and structural formulae of compounds described herein

| Compound Number | Compound Name | Structural Formula |
|---|---|---|
| T-34 | | |
| T-35 | | |
| T-36 | | |
| T-37A | | |
| T-37 | | |
| T-37B | | |
| T-38 | | |

TABLE 1-continued
Compound numbers, names, and structural formulae of compounds described herein
| Compound Number | Compound Name | Structural Formula |
|---|---|---|
| T-39 | | 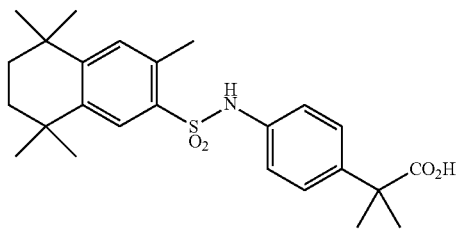 [SMILES: Cc1cc2c(cc1S(=O)(=O)Nc1ccc(C(C)(C)C(=O)O)cc1)C(C)(C)CCC2(C)C] |
| T-40 | | 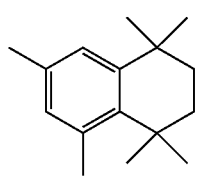 [SMILES: Cc1cc(C)c2c(c1)C(C)(C)CCC2(C)C] |
| T-41 | | 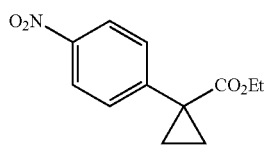 [SMILES: CCOC(=O)C1(c2ccc([N+](=O)[O-])cc2)CC1] |
| T-42 | | 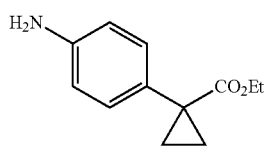 |
| T-43 | | 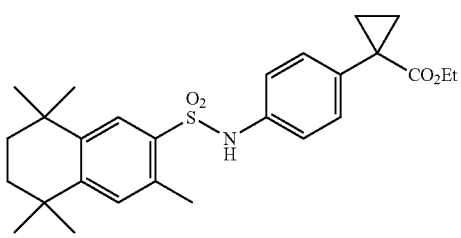 [SMILES: CCOC(=O)C1(c2ccc(NS(=O)(=O)c3cc4c(cc3C)C(C)(C)CCC4(C)C)cc2)CC1] |
| T-44 | | 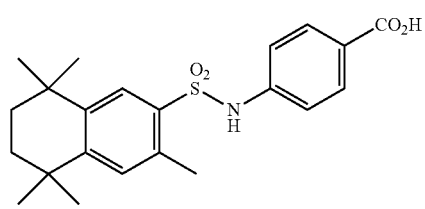 [SMILES: Cc1cc2c(cc1S(=O)(=O)Nc1ccc(C(=O)O)cc1)C(C)(C)CCC2(C)C] |
| T-45 | | 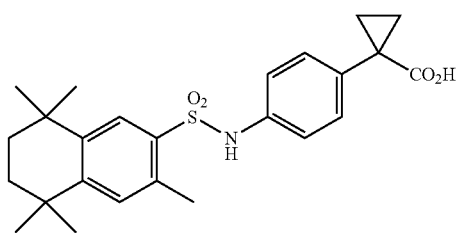 [SMILES: Cc1cc2c(cc1S(=O)(=O)Nc1ccc(C3(C(=O)O)CC3)cc1)C(C)(C)CCC2(C)C] |

TABLE 1-continued

Compound numbers, names, and structural formulae of compounds described herein

| Compound Number | Compound Name | Structural Formula |
|---|---|---|
| SS-100 | | 4-nitrophenyl diethyl ester structure (O$_2$N-C$_6$H$_4$-C(Et)(Et)-CO$_2$Et) |
| SS-101 | | 4-aminophenyl diethyl ester structure (H$_2$N-C$_6$H$_4$-C(Et)(Et)-CO$_2$Et) |
| SS-200 | | 4-nitrophenyl isopropyl ester structure (O$_2$N-C$_6$H$_4$-CH(iPr)-CO$_2$Et) |
| T-19B | | tetramethyltetrahydronaphthalene sulfonamide linked to phenyl isopropyl ester |
| SS-201 | | 4-aminophenyl isopropyl ester structure (H$_2$N-C$_6$H$_4$-CH(iPr)-CO$_2$Et) |
| 17A | | tetramethyltetrahydronaphthalene sulfonamide linked to phenyl diethyl ester |

TABLE 2

Structure and Activity Results for Compounds of Formula (1)

| Cmpd No. | Structure | IC50 26A1 (μM) | Keto IC50 (A1) | IC50 relative to keto | IC50 26B1 (μM) | Keto IC50 (B1) | IC50 relative to keto |
|---|---|---|---|---|---|---|---|
| 01 | 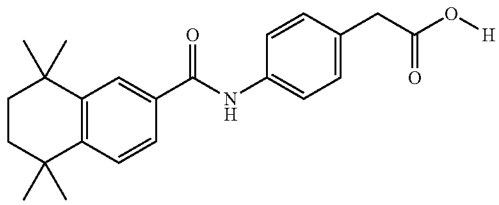 [SMILES: CC1(C)CCC(C)(C)c2cc(C(=O)Nc3ccc(CC(=O)O)cc3)ccc21] | 5.66 | 4.46 | 1.27 | 8.807 | 7.44 | 1.18 |
| 02 | 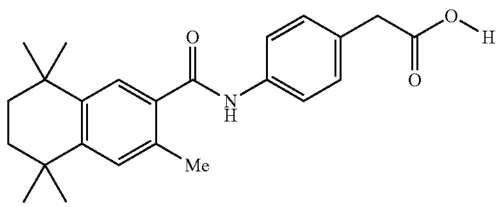 [SMILES: Cc1cc2c(cc1C(=O)Nc1ccc(CC(=O)O)cc1)C(C)(C)CCC2(C)C] | 0.83 | 4.46 | .19 | 2.061 | 7.44 | 0.28 |
| 03 | 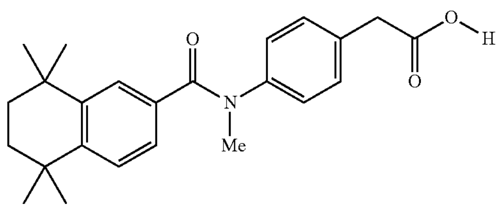 [SMILES: CN(C(=O)c1ccc2c(c1)C(C)(C)CCC2(C)C)c1ccc(CC(=O)O)cc1] | >100 | 15.66 | | 65.44 | 4.39 | 14.9 |
| 04 aka T-7 | 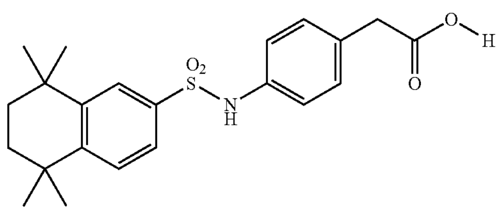 [SMILES: CC1(C)CCC(C)(C)c2cc(S(=O)(=O)Nc3ccc(CC(=O)O)cc3)ccc21] | 1.14 | 4.46 | 0.26 | 18.87 | 4.39 | 4.3 |
| 04A | 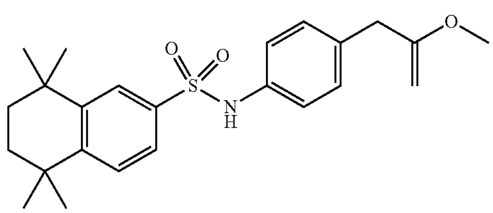 [SMILES: C=C(Cc1ccc(NS(=O)(=O)c2ccc3c(c2)C(C)(C)CCC3(C)C)cc1)OC] | 14.02 | 5.5 | | | | |
| 04B | 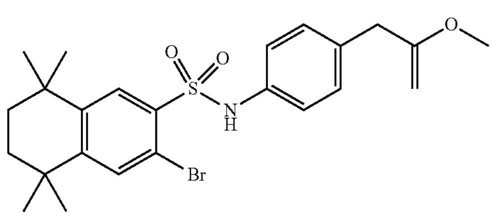 [SMILES: C=C(Cc1ccc(NS(=O)(=O)c2cc3c(cc2Br)C(C)(C)CCC3(C)C)cc1)OC] | 8.24 | 3.2 | | | | |
| 05 | 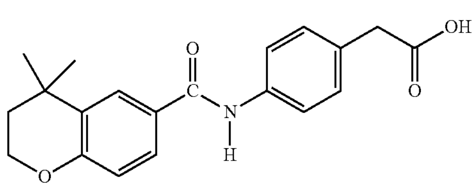 [SMILES: CC1(C)CCOc2ccc(C(=O)Nc3ccc(CC(=O)O)cc3)cc21] | 39.73 | 15.66 | 2.5 | 11.5 | 6.64 | 6.641 |

TABLE 2-continued

Structure and Activity Results for Compounds of Formula (1)

| Cmpd No. | Structure | IC50 26A1 (μM) | Keto IC50 (A1) | IC50 relative to keto | IC50 26B1 (μM) | Keto IC50 (B1) | IC50 relative to keto |
|---|---|---|---|---|---|---|---|
| 06 | 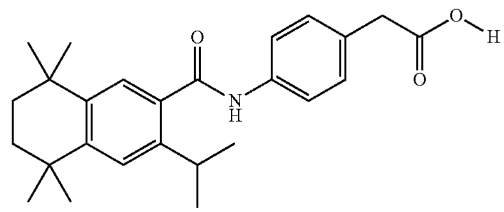 [SMILES: CC(C)c1cc2c(cc1C(=O)Nc1ccc(CC(=O)O)cc1)C(C)(C)CCC2(C)C] | 1.29 | 2.38 | 0.54 | 42.28 | 6.64 | 6.37 |
| 07 aka T-13 | 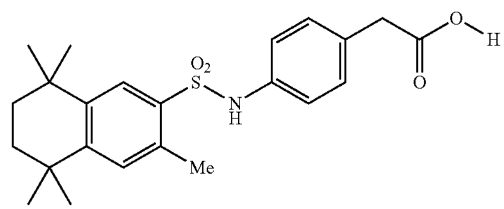 [SMILES: Cc1cc2c(cc1S(=O)(=O)Nc1ccc(CC(=O)O)cc1)C(C)(C)CCC2(C)C] | 0.47 | 2.38 | 0.2 | >1000 | 4.39 | |
| 08 | 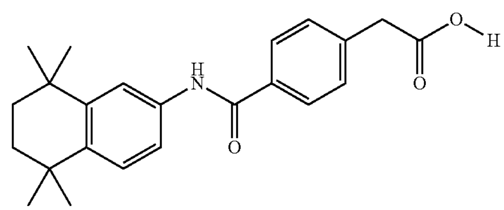 [SMILES: CC1(C)CCC(C)(C)c2cc(NC(=O)c3ccc(CC(=O)O)cc3)ccc21] | 3.17 | 2.38 | 1.33 | 19.17 | 4.39 | 4.36 |
| 09 aka T-23 | 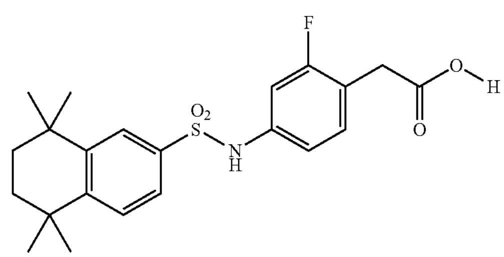 [SMILES: CC1(C)CCC(C)(C)c2cc(S(=O)(=O)Nc3ccc(CC(=O)O)c(F)c3)ccc21] | 2.2 | 1.33 | 1.65 | 14.24 | 6.64 | 2.14 |
| 09A | 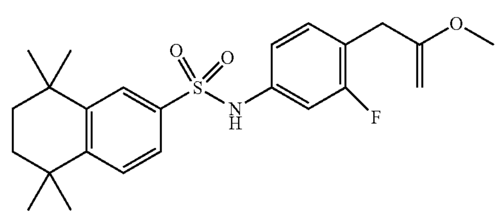 [SMILES: C=C(Cc1ccc(NS(=O)(=O)c2ccc3c(c2)C(C)(C)CCC3(C)C)cc1F)OC] | 80.52 | 31.7 | | | | |
| 10 | 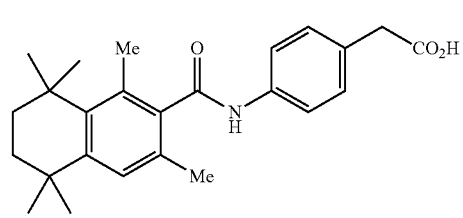 [SMILES: Cc1cc2c(c(C)c1C(=O)Nc1ccc(CC(=O)O)cc1)C(C)(C)CCC2(C)C] | 8.23 | 1.33 | 6.19 | 0.55 | 6.64 | 0.08 |
| 11 aka T-30 | 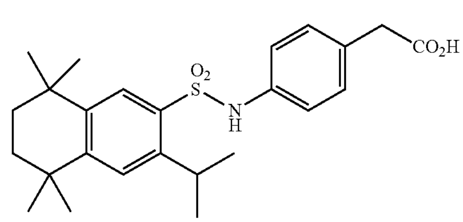 [SMILES: CC(C)c1cc2c(cc1S(=O)(=O)Nc1ccc(CC(=O)O)cc1)C(C)(C)CCC2(C)C] | 20.01 | 1.33 | 15.05 | >1000 | 6.64 | |

TABLE 2-continued

Structure and Activity Results for Compounds of Formula (1)

| Cmpd No. | Structure | IC50 26A1 (μM) | Keto IC50 (A1) | IC50 relative to keto | IC50 26B1 (μM) | Keto IC50 (B1) | IC50 relative to keto |
|---|---|---|---|---|---|---|---|
| 12 aka T-39 | 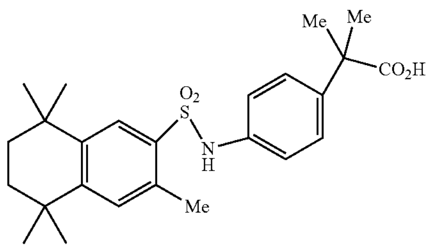 [SMILES: Cc1cc2c(cc1S(=O)(=O)Nc1ccc(C(C)(C)C(=O)O)cc1)C(C)(C)CCC2(C)C] | 0.1 | 1.33 | .08 | >1000 | 6.64 | |
| 13 aka T-45 | 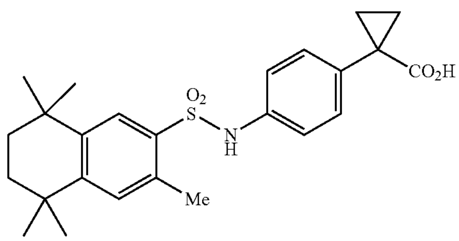 [SMILES: Cc1cc2c(cc1S(=O)(=O)Nc1ccc(C3(C(=O)O)CC3)cc1)C(C)(C)CCC2(C)C] | 6.2 | 5.84 | 1.06 | >100 | 7.97 | |
| 14 (potential agonist), aka T-44 | 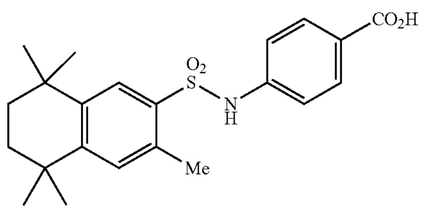 [SMILES: Cc1cc2c(cc1S(=O)(=O)Nc1ccc(C(=O)O)cc1)C(C)(C)CCC2(C)C] | 28.39 | 5.84 | 4.86 | >100 | 7.97 | |
| 14A | 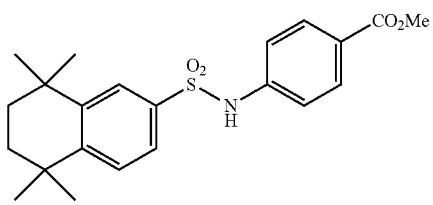 [SMILES: COC(=O)c1ccc(NS(=O)(=O)c2ccc3c(c2)C(C)(C)CCC3(C)C)cc1] | | | | | | |
| 15 (agonist) | 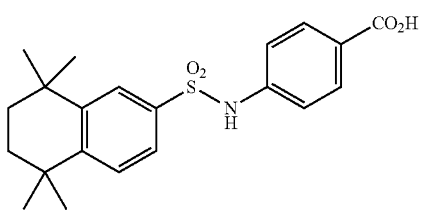 [SMILES: CC1(C)CCC(C)(C)c2cc(S(=O)(=O)Nc3ccc(C(=O)O)cc3)ccc21] | >1000 | 12.21 | | >100 | 4.25 | |
| 16 | 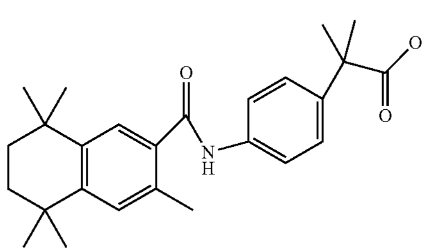 [SMILES: Cc1cc2c(cc1C(=O)Nc1ccc(C(C)(C)C(=O)O)cc1)C(C)(C)CCC2(C)C] | 1.774 | 12.21 | 0.14 | 11.92 | 4.25 | 2.8 |

TABLE 2-continued

Structure and Activity Results for Compounds of Formula (1)

| Cmpd No. | Structure | IC50 26A1 (μM) | Keto IC50 (A1) | IC50 relative to keto | IC50 26B1 (μM) | Keto IC50 (B1) | IC50 relative to keto |
|---|---|---|---|---|---|---|---|
| 17 | [structure] | 38.66 | 3.07 | 12.6 | 0.29 | 8.25 | .035 |
| 18 | [structure] | >1000 | 7.49 | | 9.066 | 6.57 | 1.38 |
| 19 | [structure] | 0.7414 | 4.77 | 0.16 | >100 | 12.16 | |
| 21 | [structure] | 1.9 | 4.8 | 0.4 | 21.8 | 2 | 10.8 |

TABLE 3

Luciferase Activity

| Treatment | RLU Avg | SD | 0.1 μM RLU Avg | SD | 1 μM RLU Avg | SD | 10 μM RLU Avg | SD |
|---|---|---|---|---|---|---|---|---|
| DMSO | 0.0079 | 0.0009 | | | | | | |
| RA | | | 0.0091 | 0.0016 | 0.0188 | 0.0016 | 0.0441 | 0.0051 |
| Cmpd 01 | | | 0.0041 | 0.0006 | 0.0053 | 0.0004 | 0.0077 | 0.0011 |
| DMSO | 0.0041 | 0.0007 | | | | | | |
| RA | | | 0.0081 | 0.0013 | 0.0168 | 0.0014 | 0.0827 | 0.0105 |
| Cmpd 02 | | | 0.004 | 0 | 0.0042 | 0.0008 | 0.0066 | 0.0003 |
| Cmpd 03 | | | 0.0041 | 0.0003 | 0.0039 | 0.0001 | 0.005 | 0.0008 |
| Cmpd 04 | | | 0.0046 | 0.0001 | 0.0035 | 0.0002 | | |
| DMSO | 0.0018 | 0.0002 | | | | | | |
| RA | | | 0.0028 | 0.0001 | 0.0091 | 0.0016 | 0.0122 | 0.0022 |
| Cmpd 06 | | | 0.0021 | 0.0004 | 0.002 | 0.0007 | 0.0018 | 0.0003 |
| Cmpd 07 | | | 0.0016 | 0.0003 | 0.0019 | 0.0004 | 0.0011 | 0.0001 |

TABLE 3-continued

| | | | Luciferase Activity | | | | | |
|---|---|---|---|---|---|---|---|---|
| | | | 0.1 μM | | 1 μM | | 10 μM | |
| | RLU | | RLU | | RLU | | RLU | |
| Treatment | Avg | SD | Avg | SD | Avg | SD | Avg | SD |
| Cmpd 08 | | | 0.0025 | 0.0007 | 0.0019 | 0.0006 | 0.0028 | 0.0001 |
| Cmpd 09 | | | 0.0018 | 0.0004 | 0.0017 | 0.0004 | 0.0012 | 0.0001 |
| DMSO | 0.074 | 0.003 | | | | | | |
| RA | | | 0.12 | 0.039 | 0.132 | 0.006 | 0.279 | 0.021 |
| Cmpd 010 | | | 0.073 | 0.019 | 0.076 | 0.004 | 0.084 | 0.008 |
| Cmpd 011 | | | 0.064 | 0.005 | 0.062 | 0.002 | 0.044 | 0.016 |
| Cmpd 012 | | | 0.067 | 0.007 | 0.082 | 0.012 | 0.041 | 0.002 |
| DMSO | 0.087 | 0.014 | | | | | | |
| RA | | | 0.088 | 0.016 | 0.162 | 0.017 | 0.193 | 0.045 |
| Cmpd 013 | | | 0.113 | 0.026 | 0.07 | 0.01 | 0.04 | 0.003 |
| DMSO | 0.133 | 0.011 | | | | | | |
| RA | | | 0.26 | 0.037 | 0.327 | 0.005 | 0.747 | 0.118 |
| Cmpd 014 | | | 0.111 | 0.004 | 0.125 | 0.01 | 0.134 | 0.007 |
| Cmpd 015 | | | 0.129 | 0.018 | 0.212 | 0.03 | 0.816 | 0.133 |
| DMSO | 0.211 | 0.041 | | | | | | |
| RA | | | 0.26 | 0.037 | 0.327 | 0.005 | 0.747 | 0.118 |
| Cmpd 016 | | | 0.166 | 0.036 | 0.183 | 0.03 | 0.155 | 0.036 |
| DMSO | 0.0293 | 0.0021 | | | | | | |
| RA | | | 0.0353 | 0.0025 | 0.059 | 0.0026 | 0.1277 | 0.0093 |
| Cmpd 017 | | | 0.023 | 0.0035 | 0.026 | 0.0035 | 0.038 | 0.0062 |
| DMSO | 0.0853 | 0.0196 | | | | | | |
| RA | | | 0.1073 | 0.006 | 0.1653 | 0.015 | 0.528 | 0.0701 |
| Cmpd 018 | | | 0.0683 | 0.0083 | 0.0597 | 0.0042 | 0.05 | 0.0053 |
| DMSO | 0.0248 | 0.0087 | | | | | | |
| RA | | | 0.0214 | 0.0027 | 0.0309 | 0.0027 | 0.126 | 0.0178 |
| Cmpd 019 | | | 0.0244 | 0.0052 | 0.019 | 0.0102 | 0.0076 | 0.003 |

The invention claimed is:

1. A method of treating a disease or condition that is responsive to retinoic acid or a derivative thereof in a mammal, comprising administering an inhibitor of the breakdown of retinoic acid (RA), comprising a compound of Formula (1)

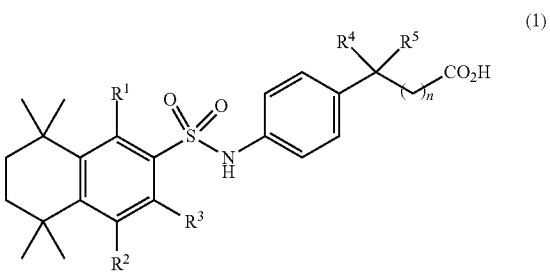

where $R^1$, $R^2$, and $R^3$ are independently H or $C_1$—$C_4$; $R^4$ and $R^5$ are independently H or $C_1$ and when $R^4$ and $R^5$ are each $C_1$ they optionally form a ring; and n is 0 to 4.

2. The method of claim 1, wherein the disease or condition is a skin disease.

3. The method of claim 2, wherein the skin disease is actinic keratosis, arsenic keratosis, inflammatory and non-inflammatory acne, psoriasis, ichthyosis and other keratinization, hyperproliferative disorders of the skin, eczema, atopic dermatitis, Darriers disease, lichen planus, glucocorticoid damage, or steroid atrophy.

4. The method of claim 1 or 2, wherein the compound is applied as a topical antimicrobial, a skin anti pigmentation agent, to treat and reverse the effects of age and photo damage to the skin.

5. The method of claim 1, wherein the condition is premalignant or malignant hyperprolifertive diseases, cancer of the breast, skin, prostate, cervix, uterus, colon, bladder, esophagus, stomach, lung, larynx, oral cavity, blood, lymphatic system, metaplasias, dysplasias, neoplasias, leukoplasias, or papillomas of the mucous membranes, or Kaposi's sarcoma.

6. The method of claim 1, wherein the compound is useful to treat diseases of the eye comprising prolieferative vitreoretinopathy (PVR), retinal detachment, dry eye, corneopathies.

7. The method of claim 1, wherein the compound is useful to treat cardiovascular disease.

8. The method of claim 7, wherein the cardiovascular disease comprises diseases associated with lipid metabolism, dyslipidemias, prevention of post-angioplasty restenosis.

9. The method of claim 1, wherein the compound is useful as an agent to increase the level of circulating tissue plasminogen activator (TPA), or to treat conditions and diseases associated with: human papilloma virus $(HPV)_1$ inflammatory disease from the group consisting of pulmonary fibrosis, ileitis, colitis and Crohn's disease; neurodegenerative disease selected from the group consisting of Alzheimer's disease, Parkinson's disease, stroke; improper pituitary function including improper production of growth hormone; modulation of apoptosis including both the induction of apoptosis, and inhibition of T-cell activated apoptosis; restoration of hair growth; diseases associated with the immune system; modulation of organ transplant rejection; or facilitation of wound healing.

10. The method of claim 1, wherein the compound is useful in treating type II non-insulin dependent diabetes mellitus, disorders of ectopic bone formation, or muscle tissue calcification.

11. The method of claim 1 in the treatment of a disease or condition, wherein it is administered as a powder, spray, pill, tablet, syrup, elixir, solution or suspension capable of being administered by injection, suppository, extended release formulation for deposit under the skin or intramuscular injection.

12. The method of claim 1, wherein a compound of formula (1) is included in a medicament for topical application in a formulation comprising between 0.01 milligrams and 1 mg per mL of the compound.

13. The method of claim 1, wherein a compound of formula (1) is included in a medicament for systemic administration in a formulation comprising between 0.01 and 5 mg per kg body weight per day.

14. The method of claim 1, wherein the compound of Formula (1) is given in combination with a retinoid or a retinoid precursor selected from retinol, retinaldehyde, RA, or other natural or synthetic retinoids.

15. The method of claim 14, wherein the compounds are provided as a combination in the same tablet, capsule, injectable, or topical formulation.

16. The method of claim 1, wherein in the compound of Formula (1), $R^1$ and $R^2$ are H, and $R^3$ is methyl.

17. The method of claim 1, wherein in the compound of Formula (1), n is 1.

18. The method of claim 1, wherein in the compound of Formula (1), $R^4$ and $R^5$ are methyl.

19. The method of claim 1, wherein in the compound of Formula (1), $R^4$ and $R^5$ are each $C_1$ and they form a ring.

20. The method of claim 1, wherein in the compound of Formula (1) is:

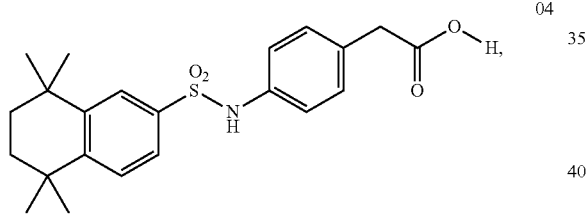

04

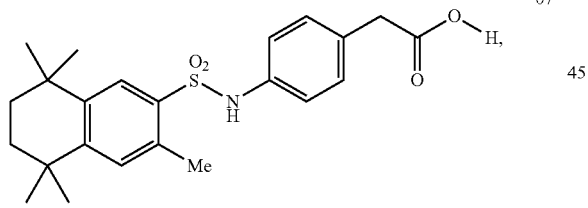

07

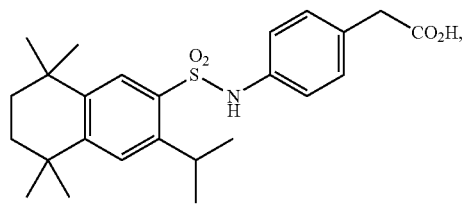

11

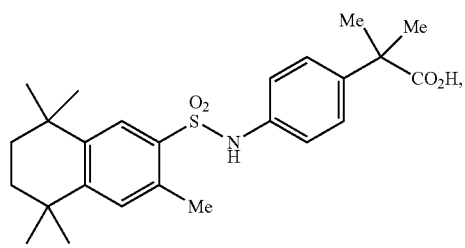

12

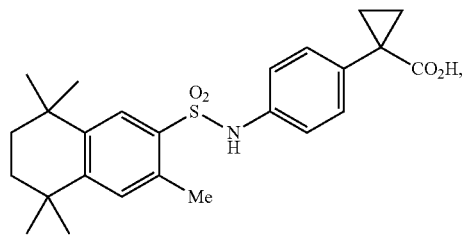

13

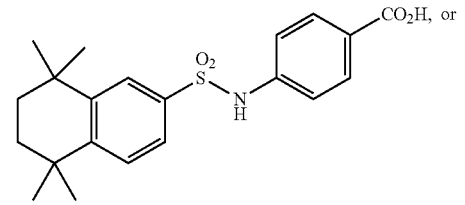

15

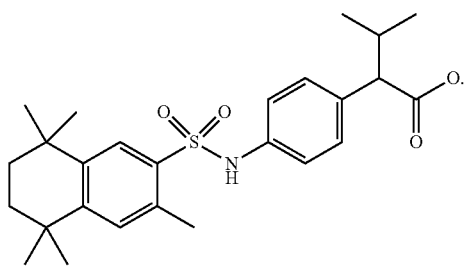

19

* * * * *